US008426147B2

(12) United States Patent
Francis-Lang et al.

(10) Patent No.: US 8,426,147 B2
(45) Date of Patent: Apr. 23, 2013

(54) RORS AS MODIFIERS OF THE P21 PATHWAY AND METHODS OF USE

(75) Inventors: Helen Francis-Lang, San Francisco, CA (US); Lori Friedman, San Carlos, CA (US); Thomas Kidd, Truckee, CA (US); Siobhan Roche, Coolock (IE); Haiguang Zhang, El Sobrante, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 12/325,914

(22) Filed: Dec. 1, 2008

(65) Prior Publication Data

US 2009/0149413 A1 Jun. 11, 2009

Related U.S. Application Data

(63) Continuation of application No. 10/528,032, filed as application No. PCT/US03/28897 on Sep. 15, 2003, now abandoned.

(60) Provisional application No. 60/411,010, filed on Sep. 16, 2002.

(51) Int. Cl.
*G01N 33/53* (2006.01)

(52) U.S. Cl.
USPC .......... 435/7.2

(58) Field of Classification Search .......... None
See application file for complete search history.

(56) References Cited

U.S. PATENT DOCUMENTS 6,812,339 B1 11/2004 Venter et al.
2002/0108138 A1* 8/2002 Guenther .......... 800/18

FOREIGN PATENT DOCUMENTS

WO WO 93/06215 A1 4/1993
WO WO 00/24757 A1 5/2000

OTHER PUBLICATIONS

Miki, N. et al.: *Homo sapiens* RAR-related orphan receptor A (RORA), transcript variant 3, mRNA. Genbank GI 19743899, Mar. 26, 2002.
Miki, N. et al.: *Homo sapiens* RAR-related orphan receptor A (RORA), transcript variant 2, mRNA. Genbank GI 19743900, Mar. 26, 2002.
Miki, N. et al.: *Homo sapiens* RAR-related orphan receptor A (RORA), transcript variant 1, mRNA. Genbank GI 19743902, Mar. 26, 2002.
Giguere, V. at al.: Human orphan hormone nuclear receptor RORalpha2 mRNA, complete cds, Genbak GI 451565, Mar. 7, 1995.
Strausberg, R.L. et al.: *Homo sapiens*, Similar to RAR-related orphan receptor alpha, clone MGC:12811 IMAGE:4121602, mRNA, complete cds. Genbank GI 14250723, Jul. 12, 2001.
Becker-Andre, M. et al.: Human transcription factor RZR-alpha mRNA, complete cds. Genbank GI 348240, Oct. 16, 1993.
Miki, N. et al.: *Homo sapiens* RAR-related orphan receptor A (RORA), transcript variant 4, mRNA. Genbank GI 19743904, Mar. 26, 2002.
Becker-Andre, M.: *H.sapiens* mRNA for nuclear orphan receptor ROR-beta. Genbank GI 1619293, Aug. 6, 1997.
Strausberg,R.L. et al.: *Homo sapiens* cDNA clone IMAGE:6141868, partial cds. Genbank GI 30704550, May 14, 2003.
Kurebayashi,S. et al.: *Homo sapiens* RAR-related orphan receptor C (RORC), mRNA. Genbank GI 19743908, Mar. 26, 2002.
Bahr, A. et al.: *Homo sapiens* mRNA; cDNA DKFZp667A0710 (from clone DKFZp667A0710); complete cds. Genbank GI 21739736, Jul. 12, 2002.
Hirose, T. et al.: Human orphan receptor ROR gamma mRNA, complete cds. Genbank GI 758419, Apr. 4, 1995.
Strausberg, R.L. et al.: *Homo sapiens*, clone MGC:34470 IMAGE:5186655, mRNA, complete cds. Genbank GI 21594879, Jun. 26, 2002.
Ota, T. et al.: *Homo sapiens* cDNA FLJ40675 fis, clone THYMU2021714, highly similar to Nuclear Receptor ROR-Gamma. Genbank GI 21757912, Jul. 15, 2002.
Miki, N. et al.: RAR-related orphan receptor A, isoform B; RAR-related orphan receptor alpha; retinoic acid receptor-related orphan receptor alpha; transcription factor RZR-alpha; ROR-alpha [*Homo sapiens*]. Genbank GI 19743901, Mar. 26, 2002.
Gawlas, K. et al.: RAR-related orphan receptor B; RAR-related orphan receptor beta; retinoic acid-binding receptor beta; nuclear receptor RZR-beta [*Homo sapiens*]. Genbank GI 19743907, Mar. 26, 2002.
Wang, H. et al.: RAR-related orphan receptor C; RAR-related orphan receptor gamma; nuclear receptor ROR-gamma; retinoic acid-binding receptor gamma [*Homo sapiens*]. Genbank GI 19743909, Mar. 26, 2002.
GenBank Reference No. 13643057, entitled: "cyclin-dependent kinase inhibitor 1A (p21, Cip1) [*Homo sapiens*]," dated Jul. 17, 2001, NCBI Annotation Project.
GenBank Reference No. 1684911, entitled "*Drosophila dacapo* cDNA coding region," de Nooij, J.C. et al., Cell, dated Nov. 23, 1996.
GenBank Reference No. 4966283, entitled: "Genome sequence of the nematode *C. elegans*: a platform for investigating biology. The *C. elegans* Sequencing Consortium," Waterston,R., Science 282 (5396), 2012-2018, dated May 23, 2002.
GenBank Reference No. 2656016, entitled: "cell cycle regulator p21 protein, Wos2p [*Schizosaccharomyces pombe*]," McDougall, R., dated Oct. 15, 1999.
Stehlin-Gaon, C. et al.: "All-trans retinoic acid is a ligand for the orphan nuclear receptor RORB," Nature Structural Biology, Oct. 2003, vol. 10, No. 10, pp. 820-825.
Wiesenberg, I. et al.: "Specific activation of the nuclear receptor PPARg and RORA by the antidiabetic thiazolidinedione BRL 49653 and the anitarthritic thiazolidinedione derivative CGP 52608," Molecular Pharmacology (1998) vol. 53, pp. 1131-1138.

* cited by examiner

*Primary Examiner* — Michael Pak
(74) *Attorney, Agent, or Firm* — McDonnell Boehnen Hulbert & Berghoff LLP

(57) ABSTRACT

Human ROR genes are identified as modulators of the p21 pathway, and thus are therapeutic targets for disorders associated with defective p21 function. Methods for identifying modulators of p21, comprising screening for agents that modulate the activity of ROR are provided.

15 Claims, No Drawings

RORS AS MODIFIERS OF THE P21 PATHWAY AND METHODS OF USE

REFERENCE TO RELATED APPLICATIONS

This application is a continuation of U.S. application Ser. No. 10/528,032 filed on Jul. 29, 2005, which is a U.S. national phase of International Application No. PCT/US03/28897 filed Sep. 15, 2003 which claims benefit under 35 U.S.C. §119(e) to application Ser. No. 60/411,010 filed Sep. 16, 2002. The contents of the prior applications are hereby incorporated in their entireties.

BACKGROUND OF THE INVENTION

The p21/CDKN1/WAF1/CIP1 protein (El-Deiry, W. S.; et al. Cell 75: 817-825, 1993; Harper, J. W.; et al. Cell 75: 805-816, 1993; Huppi, K et al. Oncogene 9: 3017-3020, 1994) is a cell cycle control protein that inhibits cyclin-kinase activity, is tightly regulated at the transcriptional level by p53, and mediates p53 suppression of tumor cell growth. Along with p53, p21 appears to be essential for maintaining the G2 checkpoint in human cells (Bunz, F.; Dutriaux, A.; et al. Science 282:1497-1501, 1998). Sequences of P21 are well-conserved throughout evolution, and have been identified in species as diverse as human (Genbank Identifier 13643057), *Drosophila melanogaster* (GI#1684911), *Caenorhabditis elegans* (GI#4966283), and yeast (GI#2656016).

RORA (retinoic acid receptor related orphan receptor A) is a member of the nuclear hormone receptor superfamily (Giguere, V., et al (1994) Genes And Development 8: 538-53). Members of this gene family include the steroid hormone, thyroid hormone and retinoid receptors, and orphan receptors for which a ligand has not yet been identified. Members of this superfamily also share a common modular structure composed of a transactivation domain, a DNA-binding domain, and a ligand-binding domain. Typically, their transcriptional transactivation function is regulated by small lipophilic molecules, such as steroid hormones, vitamin D, retinoic acids, and thyroid hormone. These molecules are synthesized in the organism and pass readily through the plasma membrane to reach the corresponding receptors inside the cell.

Mutations in the RORA gene have been related to recessive Robinow syndrome (Afzal, A. R., et al (2000) Nat Genet 25:419-22). RORB is a transcription factor and interacts with NM23-2, a nucleoside diphosphate kinase involved in organogenesis and differentiation (Paravicini, G. et al. (1996) Biochem. Biophys. Res. Commun. 227: 82-87). RORC (ROR-gamma) is important for lymphoid organogenesis and plays an important regulatory role in thymopoiesis (Kurebayashi, S. et al (2000) Proc. Nat. Acad. Sci. 97: 10132-10137).

The ability to manipulate the genomes of model organisms such as *Drosophila* provides a powerful means to analyze biochemical processes that, due to significant evolutionary conservation, have direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechler B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p21, modifier genes can be identified that may be attractive candidate targets for novel therapeutics.

All references cited herein, including patents, patent applications, publications, and sequence information in referenced Genbank identifier numbers, are incorporated herein in their entireties.

SUMMARY OF THE INVENTION

We have discovered genes that modify the p21 pathway in *Drosophila*, and identified their human orthologs, hereinafter referred to as retinoic acid receptor related orphan receptor (ROR). The invention provides methods for utilizing these p21 modifier genes and polypeptides to identify ROR-modulating agents that are candidate therapeutic agents that can be used in the treatment of disorders associated with defective or impaired p21 function and/or ROR function. Preferred ROR-modulating agents specifically bind to ROR polypeptides and restore p21 function. Other preferred ROR-modulating agents are nucleic acid modulators such as antisense oligomers and RNAi that repress ROR gene expression or product activity by, for example, binding to and inhibiting the respective nucleic acid (i.e. DNA or mRNA).

ROR modulating agents may be evaluated by any convenient in vitro or in vivo assay for molecular interaction with an ROR polypeptide or nucleic acid. In one embodiment, candidate ROR modulating agents are tested with an assay system comprising a ROR polypeptide or nucleic acid. Agents that produce a change in the activity of the assay system relative to controls are identified as candidate p21 modulating agents. The assay system may be cell-based or cell-free. ROR-modulating agents include ROR related proteins (e.g. dominant negative mutants, and biotherapeutics); ROR-specific antibodies; ROR-specific antisense oligomers and other nucleic acid modulators; and chemical agents that specifically bind to or interact with ROR or compete with ROR binding partner (e.g. by binding to an ROR binding partner). In one specific embodiment, a small molecule modulator is identified using a binding assay. In specific embodiments, the screening assay system is selected from an apoptosis assay, a cell proliferation assay, an angiogenesis assay, and a hypoxic induction assay.

In another embodiment, candidate p21 pathway modulating agents are further tested using a second assay system that detects changes in the p21 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p21 pathway, such as an angiogenic, apoptotic, or cell proliferation disorder (e.g. cancer).

The invention further provides methods for modulating the ROR function and/or the p21 pathway in a mammalian cell by contacting the mammalian cell with an agent that specifically binds a ROR polypeptide or nucleic acid. The agent may be a small molecule modulator, a nucleic acid modulator, or an antibody and may be administered to a mammalian animal predetermined to have a pathology associated the p21 pathway.

DETAILED DESCRIPTION OF THE INVENTION

A dominant loss of function screen was carried out in *Drosophila* to identify genes that interact with the cyclin dependent kinase inhibitor, p21 (Bourne H R, et al., Nature (1990) 348(6297):125-132; Marshall C J, Trends Genet (1991) 7(3):91-95). Expression of the p21 gene in the eye causes deterioration of normal eye morphology. Modifiers of the eye phenotype were identified as members of the p21 pathway. The HR46 gene was identified as a modifier of the p21 pathway. Accordingly, vertebrate orthologs of these modifiers, and preferably the human orthologs, ROR genes (i.e., nucleic acids and polypeptides) are attractive drug targets for the treatment of pathologies associated with a defective p21 signaling pathway, such as cancer.

In vitro and in vivo methods of assessing ROR function are provided herein. Modulation of the ROR or their respective binding partners is useful for understanding the association of the p21 pathway and its members in normal and disease conditions and for developing diagnostics and therapeutic modalities for p21 related pathologies. ROR-modulating agents that act by inhibiting or enhancing ROR expression, directly or indirectly, for example, by affecting an ROR function such as binding activity, can be identified using methods provided herein. ROR modulating agents are useful in diagnosis, therapy and pharmaceutical development.

Nucleic Acids and Polypeptides of the Invention

Sequences related to ROR nucleic acids and polypeptides that can be used in the invention are disclosed in Genbank (referenced by Genbank identifier (GI) number) as GI#s 19743899 (SEQ ID NO:1), 19743900 (SEQ ID NO:2), 19743902 (SEQ ID NO:3), 451565 (SEQ ID NO:4), 14250723 (SEQ ID NO:5), 348240 (SEQ ID NO:6), 19743904 (SEQ ID NO:7), 19743906 (SEQ ID NO:8), 1619293 (SEQ ID NO:9), 30704550 (SEQ ID NO:10), 19743908 (SEQ ID NO:11), 21739736 (SEQ ID NO:12), 758419 (SEQ ID NO:13), 21594879 (SEQ ID NO:14), and 21757912 (SEQ ID NO:15) for nucleic acid, and GI#s 19743901 (SEQ ID NO:16), 19743907 (SEQ ID NO:17), and 19743909 (SEQ ID NO:18) for polypeptides.

The term "ROR polypeptide" refers to a full-length ROR protein or a functionally active fragment or derivative thereof. A "functionally active" ROR fragment or derivative exhibits one or more functional activities associated with a full-length, wild-type ROR protein, such as antigenic or immunogenic activity, ability to bind natural cellular substrates, etc. The functional activity of ROR proteins, derivatives and fragments can be assayed by various methods known to one skilled in the art (Current Protocols in Protein Science (1998) Coligan et al., eds., John Wiley & Sons, Inc., Somerset, N.J.) and as further discussed below. In one embodiment, a functionally active ROR polypeptide is a ROR derivative capable of rescuing defective endogenous ROR activity, such as in cell based or animal assays; the rescuing derivative may be from the same or a different species. For purposes herein, functionally active fragments also include those fragments that comprise one or more structural domains of an ROR, such as a binding domain. Protein domains can be identified using the PFAM program (Bateman A., et al., Nucleic Acids Res, 1999, 27:260-2). For example, the zinc finger domain (PFAM 00105) of ROR from GI#s 19743901, 19743907, and 19743909 (SEQ ID NOs:16, 17, and 18, respectively) is located respectively at approximately amino acid residues 104 to 179, 8 to 83, and 29 to 104. Likewise, the Ligand-binding domain of nuclear hormone receptor domain (PFAM 00104) of SEQ ID NOs:16, 17, and 18 is located respectively at approximately amino acid residues 361 to 544, 267 to 450, and 325 to 506. Methods for obtaining ROR polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:16-18 (an ROR). In further preferred embodiments, the fragment comprises the entire functionally active domain.

The term "ROR nucleic acid" refers to a DNA or RNA molecule that encodes a ROR polypeptide. Preferably, the ROR polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with human ROR. Methods of identifying orthlogs are known in the art. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" (www.psc.edu) and references cited therein.; W. R. Pearson, 1991, Genomics 11:635-650). This algorithm can be applied to amino acid sequences by using the scoring matrix developed by Dayhoff (Dayhoff: Atlas of Protein Sequences and Structure, M. O. Dayhoff ed., 5 suppl. 3:353-358, National Biomedical Research Foundation, Washington, D.C., USA), and normalized by Gribskov (Gribskov 1986 Nucl. Acids Res. 14(6):6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs:1-15. The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs:1-15 under high stringency hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18-20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.1×SSC and 0.1% SDS (sodium dodecyl sulfate).

In other embodiments, moderately stringent hybridization conditions are used that are: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 μg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that are: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of ROR Nucleic Acids and Polypeptides ROR nucleic acids and polypeptides are useful for identifying and testing agents that modulate ROR function and for other applications related to the involvement of ROR in the p21 pathway. ROR nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of an ROR protein for assays used to assess ROR function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant ROR is expressed in a cell line known to have defective p21 function such as HCT 116 colon cancer cells available from American Type Culture Collection (ATCC), Manassas, Va.). The recombinant cells are used in cell-based screening assay systems of the invention, as described further below.

The nucleotide sequence encoding an ROR polypeptide can be inserted into any appropriate expression vector. The necessary transcriptional and translational signals, including promoter/enhancer element, can derive from the native ROR gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. An isolated host cell strain that modulates the expression of, modifies, and/or specifically processes the gene product may be used.

To detect expression of the ROR gene product, the expression vector can comprise a promoter operably linked to an ROR gene nucleic acid, one or more origins of replication, and, one or more selectable markers (e.g. thymidine kinase activity, resistance to antibiotics, etc.). Alternatively, recombinant expression vectors can be identified by assaying for the expression of the ROR gene product based on the physical or functional properties of the ROR protein in in vitro assay systems (e.g. immunoassays).

The ROR protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the ROR gene sequence is identified, the gene product can be isolated and purified using standard methods (e.g. ion exchange, affinity, and gel exclusion chromatography; centrifugation; differential solubility; electrophoresis). Alternatively, native ROR proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of ROR or other genes associated with the p21 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter ROR expression may be used in in vivo assays to test for activity of a candidate p21 modulating agent, or to further assess the role of ROR in a p21 pathway process such as apoptosis or cell proliferation. Preferably, the altered ROR expression results in a detectable phenotype, such as decreased or increased levels of cell proliferation, angiogenesis, or apoptosis compared to control animals having normal ROR expression. The genetically modified animal may additionally have altered p21 expression (e.g. p21 knockout). Preferred genetically modified animals are mammals such as primates, rodents (preferably mice or rats), among others. Preferred non-mammalian species include zebrafish, *C. elegans*, and *Drosophila*. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic *Drosophila* see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous ROR gene that results in a decrease of ROR function, preferably such that ROR expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse ROR gene is used to construct a homologous recombination vector suitable for altering an endogenous ROR gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the transgenic animal is a "knock-in" animal having an alteration in its genome that results in altered expression (e.g., increased (including ectopic) or decreased expression) of the ROR gene, e.g., by introduction of additional copies of ROR, or by operatively inserting a regulatory sequence that provides for altered expression of an endogenous copy of the ROR gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the p21 pathway, as animal models of disease and disorders implicating defective p21 function, and for in vivo testing of candidate therapeutic agents, such as those identified in screens described below. The candidate therapeutic agents are administered to a genetically modified animal having altered ROR function and phenotypic changes are compared with appropriate control animals such as genetically modified animals that receive placebo treatment, and/or animals with unaltered ROR expression that receive candidate therapeutic agent.

In addition to the above-described genetically modified animals having altered ROR function, animal models having defective p21 function (and otherwise normal ROR function), can be used in the methods of the present invention. For example, a p21 knockout mouse can be used to assess, in vivo, the activity of a candidate p21 modulating agent identified in one of the in vitro assays described below. p21 knockout mice are described in the literature (Umanoff H, et al., Proc Natl Acad Sci USA 1995 Feb. 28; 92(5):1709-13). Preferably, the candidate p21 modulating agent when administered to a model system with cells defective in p21 function, produces a detectable phenotypic change in the model system indicating that the p21 function is restored, i.e., the cells exhibit normal cell cycle progression.

Modulating Agents

The invention provides methods to identify agents that interact with and/or modulate the function of ROR and/or the p21 pathway. Modulating agents identified by the methods are also part of the invention. Such agents are useful in a variety of diagnostic and therapeutic applications associated with the p21 pathway, as well as in further analysis of the ROR protein and its contribution to the p21 pathway. Accordingly, the invention also provides methods for modulating the p21 pathway comprising the step of specifically modulating ROR activity by administering a ROR-interacting or -modulating agent.

As used herein, an "ROR-modulating agent" is any agent that modulates ROR function, for example, an agent that interacts with ROR to inhibit or enhance ROR activity or otherwise affect normal ROR function. ROR function can be affected at any level, including transcription, protein expression, protein localization, and cellular or extra-cellular activity. In a preferred embodiment, the ROR-modulating agent specifically modulates the function of the ROR. The phrases "specific modulating agent", "specifically modulates", etc., are used herein to refer to modulating agents that directly bind to the ROR polypeptide or nucleic acid, and preferably inhibit, enhance, or otherwise alter, the function of the ROR. These phrases also encompass modulating agents that alter the interaction of the ROR with a binding partner, substrate, or cofactor (e.g. by binding to a binding partner of an ROR, or to a protein/binding partner complex, and altering ROR function). In a further preferred embodiment, the ROR-modulating agent is a modulator of the p21 pathway (e.g. it restores and/or upregulates p21 function) and thus is also a p21-modulating agent.

Preferred ROR-modulating agents include small molecule compounds; ROR-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500 daltons. This class of modulators includes chemically synthesized molecules, for instance, compounds from combinatorial chemical libraries. Synthetic compounds may be rationally designed or identified based on known or inferred properties of the ROR protein or may be identified by screening compound libraries. Alternative appropriate modulators of this class are natural products, particularly secondary metabolites from organisms such as plants or fungi, which can also be identified by screening compound libraries for ROR-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the p21 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific ROR-interacting proteins are useful in a variety of diagnostic and therapeutic applications related to the p21 pathway and related disorders, as well as in validation assays for other ROR-modulating agents. In a preferred embodiment, ROR-interacting proteins affect normal ROR function, including transcription, protein expression, protein localization, and cellular or extra-cellular activity. In another embodiment, ROR-interacting proteins are useful in detecting and providing information about the function of ROR proteins, as is relevant to p21 related disorders, such as cancer (e.g., for diagnostic means).

An ROR-interacting protein may be endogenous, i.e. one that naturally interacts genetically or biochemically with an ROR, such as a member of the ROR pathway that modulates ROR expression, localization, and/or activity. ROR-modulators include dominant negative forms of ROR-interacting proteins and of ROR proteins themselves. Yeast two-hybrid and variant screens offer preferred methods for identifying endogenous ROR-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R 3rd, Trends Genet (2000) 16:5-8).

An ROR-interacting protein may be an exogenous protein, such as an ROR-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). ROR antibodies are further discussed below.

In preferred embodiments, an ROR-interacting protein specifically binds an ROR protein. In alternative preferred embodiments, an ROR-modulating agent binds an ROR substrate, binding partner, or cofactor.

Antibodies

In another embodiment, the protein modulator is an ROR specific antibody agonist or antagonist. The antibodies have therapeutic and diagnostic utilities, and can be used in screening assays to identify ROR modulators. The antibodies can also be used in dissecting the portions of the ROR pathway responsible for various cellular responses and in the general processing and maturation of the ROR.

Antibodies that specifically bind ROR polypeptides can be generated using known methods. Preferably the antibody is specific to a mammalian ortholog of ROR polypeptide, and more preferably, to human ROR. Antibodies may be polyclonal, monoclonal (mAbs), humanized or chimeric antibodies, single chain antibodies, Fab fragments, F(ab').sub.2 fragments, fragments produced by a FAb expression library, anti-idiotypic (anti-Id) antibodies, and epitope-binding fragments of any of the above. Epitopes of ROR which are particularly antigenic can be selected, for example, by routine screening of ROR polypeptides for antigenicity or by applying a theoretical method for selecting antigenic regions of a protein (Hopp and Wood (1981), Proc. Nati. Acad. Sci. U.S.A. 78:3824-28; Hopp and Wood, (1983) Mol. Immunol. 20:483-89; Sutcliffe et al., (1983) Science 219:660-66) to the amino acid sequence shown in any of SEQ ID NOs:16-18. Monoclonal antibodies with affinities of $10^8$ $M^{-1}$ preferably $10^9$ $M^{-1}$ to $10^{10}$ $M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of ROR or substantially purified fragments thereof. If ROR fragments are used, they preferably comprise at least 10, and more preferably, at least 20 contiguous amino acids of an ROR protein. In a particular embodiment, ROR-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of ROR-specific antibodies is assayed by an appropriate assay such as a solid phase enzyme-linked immunosorbant assay (ELISA) using immobilized corresponding ROR polypeptides. Other assays, such as radioimmunoassays or fluorescent assays might also be used.

Chimeric antibodies specific to ROR polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRs) (Carlos, T. M., J. M. Harlan. 1994. Blood 84:2068-2101) of mouse antibodies into a background of human framework regions and constant regions by recombinant DNA technology (Riechmann L M, et al., 1988 Nature 323: 323-327). Humanized antibodies contain ~10% murine sequences and ~90% human sequences, and thus further reduce or eliminate immunogenicity, while retaining the antibody specificities (Co M S, and Queen C. 1991 Nature 351: 501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

ROR-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Specific Biotherapeutics

In a preferred embodiment, an ROR-interacting protein may have biotherapeutic applications. Biotherapeutic agents formulated in pharmaceutically acceptable carriers and dosages may be used to activate or inhibit signal transduction pathways. This modulation may be accomplished by binding a ligand, thus inhibiting the activity of the pathway; or by binding a receptor, either to inhibit activation of, or to activate, the receptor. Alternatively, the biotherapeutic may itself be a ligand capable of activating or inhibiting a receptor. Biotherapeutic agents and methods of producing them are described in detail in U.S. Pat. No. 6,146,628.

ROR, its ligand(s), antibodies to the ligand(s) or the ROR itself may be used as biotherapeutics to modulate the activity of ROR in the p21 pathway.

Nucleic Acid Modulators

Other preferred ROR-modulating agents comprise nucleic acid molecules, such as antisense oligomers or double stranded RNA (dsRNA), which generally inhibit ROR activity. Preferred nucleic acid modulators interfere with the function of the ROR nucleic acid such as DNA replication, transcription, translocation of the ROR RNA to the site of protein translation, translation of protein from the ROR RNA, splicing of the ROR RNA to yield one or more mRNA species, or catalytic activity which may be engaged in or facilitated by the ROR RNA.

In one embodiment, the antisense oligomer is an oligonucleotide that is sufficiently complementary to an ROR mRNA to bind to and prevent translation, preferably by binding to the 5' untranslated region. ROR-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphodiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.:7:187-95; U.S. Pat. No. 5,235,033; and U.S. Pat. No. 5,378,841).

Alternative preferred ROR nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, an ROR-specific nucleic acid modulator is used in an assay to further elucidate the role of the ROR in the p21 pathway, and/or its relationship to other members of the pathway. In another aspect of the invention, an ROR-specific antisense oligomer is used as a therapeutic agent for treatment of p21-related disease states.

Assay Systems

The invention provides assay systems and screening methods for identifying specific modulators of ROR activity. As used herein, an "assay system" encompasses all the components required for performing and analyzing results of an assay that detects and/or measures a particular event. In general, primary assays are used to identify or confirm a modulator's specific biochemical or molecular effect with respect to the ROR nucleic acid or protein. In general, secondary assays further assess the activity of a ROR modulating agent identified by a primary assay and may confirm that the modulating agent affects ROR in a manner relevant to the p21 pathway. In some cases, ROR modulators will be directly tested in a secondary assay.

In a preferred embodiment, the screening method comprises contacting a suitable assay system comprising an ROR polypeptide or nucleic acid with a candidate agent under conditions whereby, but for the presence of the agent, the system provides a reference activity (e.g. binding activity), which is based on the particular molecular event the screening method detects. A statistically significant difference between the agent-biased activity and the reference activity indicates that the candidate agent modulates ROR activity, and hence the p21 pathway. The ROR polypeptide or nucleic acid used in the assay may comprise any of the nucleic acids or polypeptides described above.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicty and changes in cellular morphology or other cellular characteristics. Appropriate screening assays may use a wide range of detection methods including fluorescent, radioactive, calorimetric, spectrophotometric, and amperometric methods, to provide a read-out for the particular molecular event detected.

Cell-based screening assays usually require systems for recombinant expression of ROR and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when ROR-interacting proteins are used in screens to identify small molecule modulators, the binding specificity of the interacting protein to the ROR protein may be assayed by various known methods such as substrate processing (e.g. ability of the candidate ROR-specific binding agents to function as negative effectors in ROR-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit ROR specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a ROR polypeptide, a fusion protein thereof, or to cells or membranes bearing the polypeptide or fusion protein. The ROR polypeptide can be full length or a fragment thereof that retains functional ROR activity. The ROR polypeptide may be fused to another polypeptide, such as a peptide tag for detection or anchoring, or to another tag. The ROR polypeptide is preferably human ROR, or is an ortholog or derivative thereof as described above. In a preferred embodiment, the screening assay detects candidate agent-based modulation of ROR interaction with a binding target, such as an endogenous or exogenous protein or other substrate that has ROR-specific binding activity, and can be used to assess normal ROR gene function.

Suitable assay formats that may be adapted to screen for ROR modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate ROR and p21 pathway modulators (e.g. U.S. Pat. Nos. 5,550,019 and 6,133,437 (apoptosis assays); and U.S. Pat. Nos. 5,976,782, 6,225,118 and 6,444,434 (angiogenesis assays), among others). Specific preferred assays are described in more detail below.

Nuclear receptors (NRs) are a superfamily of ligand-dependent transcription factors that mediate the effects of hormones and other endogenous ligands to regulate the expression of specific genes. High throughput assays for nuclear receptors include fluorescent polarization binding assays (Lin S, et al. (2002) Anal Biochem 300(1):15-21), and homogeneous time-resolved fluorescence energy transfer (Zhou G, et al. (2001) Methods 25:54-61), among others.

Apoptosis Assays.

Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). Other cell-based apoptosis assays include the caspase-3/7 assay and the cell death nucleosome ELISA assay. The caspase 3/7 assay is based on the activation of the caspase cleavage activity as part of a cascade of events that occur during programmed cell death in many apoptotic pathways. In the caspase 3/7 assay (commercially available Apo-ONE™ Homogeneous Caspase-3/7 assay from Promega, cat#67790), lysis buffer and caspase substrate are mixed and added to cells. The caspase substrate becomes fluorescent when cleaved by active caspase 3/7. The nucleosome ELISA assay is a general cell death assay known to those skilled in the art, and available commercially (Roche, Cat#1774425). This assay is a quantitative sandwich-enzyme-immunoassay which uses monoclonal antibodies directed against DNA and histones respectively, thus specifically determining amount of mono- and oligonucleosomes in the cytoplasmic fraction of cell lysates. Mono and oligonucleosomes are enriched in the cytoplasm during apoptosis due to the fact that DNA fragmentation occurs several hours before the plasma membrane breaks down, allowing for accumalation in the cytoplasm. Nucleosomes are not present in the cytoplasmic fraction of cells that are not undergoing apoptosis. An apoptosis assay system may comprise a cell that expresses an ROR, and that optionally has defective p21 function (e.g. p21 is over-expressed or under-expressed relative to wild-type cells). A test agent can be added to the apoptosis assay system and changes in induction of apoptosis relative to controls where no test agent is added, identify candidate p21 modulating agents. In some embodiments of the invention, an apoptosis assay may be used as a secondary assay to test a candidate p21 modulating agents that is initially identified using a cell-free assay system. An apoptosis assay may also be used to test whether ROR function plays a direct role in apoptosis. For example, an apoptosis assay may be performed on cells that over- or under-express ROR relative to wild type cells. Differences in apoptotic response compared to wild type cells suggests that the ROR plays a direct role in the apoptotic response. Apoptosis assays are described further in U.S. Pat. No. 6,133,437.

Cell Proliferation and Cell Cycle Assays.

Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell proliferation is also assayed via phospho-histone H3 staining, which identifies a cell population undergoing mitosis by phosphorylation of histone H3. Phosphorylation of histone H3 at serine 10 is detected using an antibody specific to the phosphorylated form of the serine 10 residue of histone H3. (Chadlee, D. N. 1995, J. Biol. Chem 270:20098-105). Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman L S 3800 Liquid Scintillation Counter). Another proliferation assay uses the dye Alamar Blue (available from Biosource International), which fluoresces when reduced in living cells and provides an indirect measurement of cell number (Voytik-Harbin S L et al., 1998, In Vitro Cell Dev Biol Anim 34:239-46). Yet another proliferation assay, the MTS assay, is based on in vitro cytotoxicity assessment of industrial chemicals, and uses the soluble tetrazolium salt, MTS. MTS assays are commercially available, for example, the Promega CellTiter 96® AQueous Non-Radioactive Cell Proliferation Assay (Cat.# G5421).

Cell proliferation may also be assayed by colony formation in soft agar (Sambrook et al., Molecular Cloning, Cold Spring Harbor (1989)). For example, cells transformed with ROR are seeded in soft agar plates, and colonies are measured and counted after two weeks incubation.

Cell proliferation may also be assayed by measuring ATP levels as indicator of metabolically active cells. Such assays are commercially available, for example Cell Titer-Glo™, which is a luminescent homogeneous assay available from Promega.

Involvement of a gene in the cell cycle may be assayed by flow cytometry (Gray J W et al. (1986) Int J Radiat Biol Relat Stud Phys Chem Med 49:237-55). Cells transfected with an ROR may be stained with propidium iodide and evaluated in a flow cytometer (available from Becton Dickinson), which indicates accumulation of cells in different stages of the cell cycle.

Accordingly, a cell proliferation or cell cycle assay system may comprise a cell that expresses an ROR, and that optionally has defective p21 function (e.g. p21 is over-expressed or under-expressed relative to wild-type cells). A test agent can be added to the assay system and changes in cell proliferation or cell cycle relative to controls where no test agent is added, identify candidate p21 modulating agents. In some embodiments of the invention, the cell proliferation or cell cycle assay may be used as a secondary assay to test a candidate p21 modulating agents that is initially identified using another assay system such as a cell-free assay system. A cell proliferation assay may also be used to test whether ROR function plays a direct role in cell proliferation or cell cycle. For example, a cell proliferation or cell cycle assay may be performed on cells that over- or under-express ROR relative to wild type cells. Differences in proliferation or cell cycle compared to wild type cells suggests that the ROR plays a direct role in cell proliferation or cell cycle.

Angiogenesis.

Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel® (Becton Dickinson). Accordingly, an angiogenesis assay system may comprise a cell that expresses an ROR, and that optionally has defective p21 function (e.g. p21 is over-expressed or under-expressed relative to wild-type cells). A test agent can be added to the angiogenesis assay system and changes in angiogenesis relative to controls where no test agent is added, identify candidate p21 modulating agents. In some embodiments of the invention, the angiogenesis assay may be used as a secondary assay to test a candidate p21 modulating agents that is initially identified using another assay system. An angiogenesis assay may also be used to test whether ROR function plays a direct role in cell proliferation. For example, an angiogenesis assay may be performed on cells that over- or under-express ROR relative to wild type cells. Differences in angiogenesis compared to wild type cells suggests that the ROR plays a direct role in angiogenesis. U.S. Pat. Nos. 5,976,782, 6,225,118 and 6,444,434, among others, describe various angiogenesis assays.

Hypoxic Induction.

The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glyolytic enzymes and VEGF. Induction of such genes by hypoxic conditions may be assayed by growing cells transfected with ROR in hypoxic conditions (such as with 0.1% O2, 5% CO2, and balance N2, generated in a Napco 7001 incubator (Precision Scientific)) and normoxic conditions, followed by assessment of gene activity or expression by Taqman®. For example, a hypoxic induction assay system may comprise a cell that expresses an ROR, and that optionally has defective p21 function (e.g. p21 is over-expressed or under-expressed relative to wild-type cells). A test agent can be added to the hypoxic induction assay system and changes in hypoxic response relative to controls where no test agent is added, identify candidate p21 modulating agents. In some embodiments of the invention, the hypoxic induction assay may be used as a secondary assay to test a candidate p21 modulating agents that is initially identified using another assay system. A hypoxic induction assay may also be used to test whether ROR function plays a direct role in the hypoxic response. For example, a hypoxic induction assay may be performed on cells that over- or under-express ROR relative to wild type cells. Differences in hypoxic response compared to wild type cells suggests that the ROR plays a direct role in hypoxic induction.

Cell Adhesion.

Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Tubulogenesis.

Tubulogenesis assays monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. Serum represents an undefined source of growth factors. In a preferred embodiment, the assay is performed with cells cultured in serum free medium, in order to control which process or pathway a candidate agent modulates. Moreover, we have found that different target genes respond differently to stimulation with different pro-angiogenic agents, including inflammatory angiogenic factors such as TNF-alpa. Thus, in a further preferred embodiment, a tubulogenesis assay system comprises testing an ROR's response to a variety of factors, such as FGF, VEGF, phorbol myristate acetate (PMA), TNF-alpha, ephrin, etc.

Cell Migration.

An invasion/migration assay (also called a migration assay) tests the ability of cells to overcome a physical barrier and to migrate towards pro-angiogenic signals. Migration assays are known in the art (e.g., Paik J H et al., 2001, J Biol Chem 276:11830-11837). In a typical experimental set-up, cultured endothelial cells are seeded onto a matrix-coated porous lamina, with pore sizes generally smaller than typical cell size. The matrix generally simulates the environment of the extracellular matrix, as described above. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific, South San Francisco, Calif.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. As described above, a preferred assay system for migration/invasion assays comprises testing an ROR's response to a variety of pro-angiogenic factors, including tumor angiogenic and inflammatory angiogenic agents, and culturing the cells in serum free medium.

Sprouting Assay.

A sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 μl of methocel-collagen solution and pipetted into individual wells of a 24 well plate to allow collagen gel polymerization. Test agents are added after 30 min by pipetting 100 μl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

Primary Assays for Antibody Modulators

For antibody modulators, appropriate primary assays test is a binding assay that tests the antibody's affinity to and specificity for the ROR protein. Methods for testing antibody affinity and specificity are well known in the art (Harlow and Lane, 1988, 1999, supra). The enzyme-linked immunosorbant assay (ELISA) is a preferred method for detecting ROR-specific antibodies; others include FACS assays, radioimmunoassays, and fluorescent assays.

In some cases, screening assays described for small molecule modulators may also be used to test antibody modulators.

Primary Assays for Nucleic Acid Modulators

For nucleic acid modulators, primary assays may test the ability of the nucleic acid modulator to inhibit or enhance ROR gene expression, preferably mRNA expression. In general, expression analysis comprises comparing ROR expression in like populations of cells (e.g., two pools of cells that endogenously or recombinantly express ROR) in the presence and absence of the nucleic acid modulator. Methods for analyzing mRNA and protein expression are well known in the art. For instance, Northern blotting, slot blotting, ribonuclease protection, quantitative RT-PCR (e.g., using the TaqMan®, PE Applied Biosystems), or microarray analysis may be used to confirm that ROR mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the ROR protein or specific peptides. A variety of means including Western blotting, ELISA, or in situ detection, are available (Harlow E and Lane D, 1988 and 1999, supra).

In some cases, screening assays described for small molecule modulators, particularly in assay systems that involve ROR mRNA expression, may also be used to test nucleic acid modulators.

Secondary Assays

Secondary assays may be used to further assess the activity of ROR-modulating agent identified by any of the above methods to confirm that the modulating agent affects ROR in a manner relevant to the p21 pathway. As used herein, ROR-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with ROR.

Secondary assays generally compare like populations of cells or animals (e.g., two pools of cells or animals that endogenously or recombinantly express ROR) in the presence and absence of the candidate modulator. In general, such assays test whether treatment of cells or animals with a candidate ROR-modulating agent results in changes in the p21 pathway in comparison to untreated (or mock- or placebo-treated) cells or animals. Certain assays use "sensitized genetic backgrounds", which, as used herein, describe cells or animals engineered for altered expression of genes in the p21 or interacting pathways.

Cell-Based Assays

Cell based assays may use a mammalian cell line known to have defective p21 function such as HCT116 colon cancer cells available from American Type Culture Collection (ATCC), Manassas, Va.). Cell based assays may detect endogenous p21 pathway activity or may rely on recombinant expression of p21 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p21 pathway may be used to test candidate ROR modulators. Models for defective p21 pathway typically use genetically modified animals that have been engineered to mis-express (e.g., over-express or lack expression in) genes involved in the p21 pathway. Assays generally require systemic delivery of the candidate modulators, such as by oral administration, injection, etc.

In a preferred embodiment, p21 pathway activity is assessed by monitoring neovascularization and angiogenesis. Animal models with defective and normal p21 are used to test the candidate modulator's affect on ROR in Matrigel® assays. Matrigel® is an extract of basement membrane proteins, and is composed primarily of laminin, collagen IV, and heparin sulfate proteoglycan. It is provided as a sterile liquid at 4° C., but rapidly forms a solid gel at 37° C. Liquid Matrigel® is mixed with various angiogenic agents, such as bFGF and VEGF, or with human tumor cells which over-express the ROR. The mixture is then injected subcutaneously (SC) into female athymic nude mice (Taconic, Germantown, N.Y.) to support an intense vascular response. Mice with Matrigel® pellets may be dosed via oral (PO), intraperitoneal (IP), or intravenous (IV) routes with the candidate modulator. Mice are euthanized 5-12 days post-injection, and the Matrigel® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on ROR is assessed via tumorigenicity assays. Tumor xenograft assays are known in the art (see, e.g., Ogawa K et al., 2000, Oncogene 19:6043-6052). Xenografts are typically implanted SC into female athymic mice, 6-7 week old, as single cell suspensions either from a pre-existing tumor or from in vitro culture. The tumors which express the ROR endogenously are injected in the flank, $1\times10^5$ to $1\times10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

In another preferred embodiment, tumorogenicity is monitored using a hollow fiber assay, which is described in U.S. Pat. No. 5,698,413. Briefly, the method comprises implanting into a laboratory animal a biocompatible, semi-permeable encapsulation device containing target cells, treating the laboratory animal with a candidate modulating agent, and evaluating the target cells for reaction to the candidate modulator. Implanted cells are generally human cells from a pre-existing tumor or a tumor cell line. After an appropriate period of time, generally around six days, the implanted samples are harvested for evaluation of the candidate modulator. Tumorogenicity and modulator efficacy may be evaluated by assaying the quantity of viable cells present in the macrocapsule, which can be determined by tests known in the art, for example, MTT dye conversion assay, neutral red dye uptake, trypan blue staining, viable cell counts, the number of colonies formed in soft agar, the capacity of the cells to recover and replicate in vitro, etc.

In another preferred embodiment, a tumorogenicity assay use a transgenic animal, usually a mouse, carrying a dominant oncogene or tumor suppressor gene knockout under the control of tissue specific regulatory sequences; these assays are generally referred to as transgenic tumor assays. In a preferred application, tumor development in the transgenic model is well characterized or is controlled. In an exemplary model, the "RIP1-Tag2" transgene, comprising the SV40 large T-antigen oncogene under control of the insulin gene regulatory regions is expressed in pancreatic beta cells and results in islet cell carcinomas (Hanahan D, 1985, Nature 315:115-122; Parangi S et al, 1996, Proc Natl Acad Sci USA 93: 2002-2007; Bergers G et al, 1999, Science 284:808-812).

An "angiogenic switch," occurs at approximately five weeks, as normally quiescent capillaries in a subset of hyperproliferative islets become angiogenic. The RIP1-TAG2 mice die by age 14 weeks. Candidate modulators may be administered at a variety of stages, including just prior to the angiogenic switch (e.g., for a model of tumor prevention), during the growth of small tumors (e.g., for a model of intervention), or during the growth of large and/or invasive tumors (e.g., for a model of regression). Tumorogenicity and modulator efficacy can be evaluating life-span extension and/or tumor characteristics, including number of tumors, tumor size, tumor morphology, vessel density, apoptotic index, etc.

Diagnostic and Therapeutic Uses

Specific ROR-modulating agents are useful in a variety of diagnostic and therapeutic applications where disease or disease prognosis is related to defects in the p21 pathway, such as angiogenic, apoptotic, or cell proliferation disorders. Accordingly, the invention also provides methods for modulating the p21 pathway in a cell, preferably a cell pre-determined to have defective or impaired p21 function (e.g. due to overexpression, underexpression, or misexpression of p21, or due to gene mutations), comprising the step of administering an agent to the cell that specifically modulates ROR activity. Preferably, the modulating agent produces a detectable phenotypic change in the cell indicating that the p21 function is restored. The phrase "function is restored", and equivalents, as used herein, means that the desired phenotype is achieved, or is brought closer to normal compared to untreated cells. For example, with restored p21 function, cell proliferation and/or progression through cell cycle may normalize, or be brought closer to normal relative to untreated cells. The invention also provides methods for treating disorders or disease associated with impaired p21 function by administering a therapeutically effective amount of an ROR-modulating agent that modulates the p21 pathway. The invention further provides methods for modulating ROR function in a cell, preferably a cell pre-determined to have defective or impaired ROR function, by administering an ROR-modulating agent. Additionally, the invention provides a method for treating disorders or disease associated with impaired ROR function by administering a therapeutically effective amount of an ROR-modulating agent.

The discovery that ROR is implicated in p21 pathway provides for a variety of methods that can be employed for the diagnostic and prognostic evaluation of diseases and disorders involving defects in the p21 pathway and for the identification of subjects having a predisposition to such diseases and disorders.

Various expression analysis methods can be used to diagnose whether ROR expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective p21 signaling that express an ROR, are identified as amenable to treatment with an ROR modulating agent. In a preferred application, the p21 defective tissue overexpresses an ROR relative to normal tissue. For example, a Northern blot analysis of mRNA from tumor and normal cell lines, or from tumor and matching normal tissue samples from the same patient, using full or partial ROR cDNA sequences as probes, can determine whether particular tumors express or overexpress ROR. Alternatively, the TaqMan® is used for quantitative RT-PCR analysis of ROR expression in cell lines, normal tissues and tumor samples (PE Applied Biosystems).

Various other diagnostic methods may be performed, for example, utilizing reagents such as the ROR oligonucleotides, and antibodies directed against an ROR, as described above for: (1) the detection of the presence of ROR gene mutations, or the detection of either over- or under-expression of ROR mRNA relative to the non-disorder state; (2) the detection of either an over- or an under-abundance of ROR gene product relative to the non-disorder state; and (3) the detection of perturbations or abnormalities in the signal transduction pathway mediated by ROR.

Thus, in a specific embodiment, the invention is drawn to a method for diagnosing a disease or disorder in a patient that is associated with alterations in ROR expression, the method comprising: a) obtaining a biological sample from the patient; b) contacting the sample with a probe for ROR expression; c) comparing results from step (b) with a control; and d) determining whether step (c) indicates a likelihood of the disease or disorder. Preferably, the disease is cancer, most preferably a cancer as shown in TABLE 1. The probe may be either DNA or protein, including an antibody.

EXAMPLES

The following experimental section and examples are offered by way of illustration and not by way of limitation.

I. *Drosophila* p21 Screen

A dominant loss of function screen was carried out in *Drosophila* to identify genes that interact with the cyclin dependent kinase inhibitor, p21 (Bourne H R, et al., Nature (1990) 348(6297):125-132; Marshall C J, Trends Genet (1991) 7(3):91-95). Expression of the p21 gene from GMR-p21 transgene (Hay, B. A., et al. (1994) Development 120: 2121-2129) in the eye causes deterioration of normal eye morphology, resulting in reduced, rough eyes. Flies carrying this transgene were maintained as a stock (P 1025 F, genotype: y w; P{p21-pExp-gl-w[+]Hsp70(3'UTR)-5}). Females of this stock were crossed to a collection of males carrying piggyBac insertions (Fraser M et al., Virology (1985) 145: 356-361). Resulting progeny carrying both the transgene and transposons were scored for the effect of the transposon on the eye phenotype, i.e. whether the transposon enhanced or suppressed (or had no effect) the eye phenotype. All data was recorded and all modifiers were retested with a repeat of the original cross, and the retests were scored at least twice. Modifiers of the eye phenotype were identified as members of the p21 pathway. HR46 was an enhancer of the eye phenotype. Orthologs of the modifiers are referred to herein as ROR.

BLAST analysis (Altschul et al., supra) was employed to identify orthologs of *Drosophila* modifiers. For example, representative sequences from ROR, GI#s 19743901, 19743907, and 19743909 (SEQ ID NOs:16, 17, and 18, respectively) share 37%, 39%, and 36% amino acid identity, respectively, with the *Drosophila* HR46.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2), SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and clust (Remm M, and Sonnhammer E. Classification of transmembrane protein families in the Caenorhabditis elegans genome and identification of human orthologs. Genome Res. 2000 November; 10(11):1679-89) programs. For example, the zinc finger domain (PFAM 00105) of ROR from GI#s 19743901, 19743907, and 19743909 (SEQ ID NOs:16, 17, and 18, respectively) is located respectively at approximately amino acid residues 104 to 179, 8 to 83, and 29 to 104. Likewise, the Ligand-binding domain of nuclear hormone receptor domain (PFAM 00104) of SEQ ID NOs:16, 17, and 18 is located respectively at approximately amino acid residues 361 to 544, 267 to 450, and 325 to 506.

II. High-Throughput In Vitro Fluorescence Polarization Assay

Fluorescently-labeled ROR peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of ROR activity.

III. High-Throughput In Vitro Binding Assay.

$^{33}$P-labeled ROR peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p21 modulating agents.

IV. Immunoprecipitations and Immunoblotting

For coprecipitation of transfected proteins, $3\times10^6$ appropriate recombinant cells containing the ROR proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 μl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Expression Analysis

All cell lines used in the following experiments are NCI (National Cancer Institute) lines, and are available from ATCC (American Type Culture Collection, Manassas, Va. 20110-2209). Normal and tumor tissues were obtained from Impath, UC Davis, Clontech, Stratagene, Ardais, Genome Collaborative, and Ambion.

TaqMan analysis was used to assess expression levels of the disclosed genes in various samples.

RNA was extracted from each tissue sample using Qiagen (Valencia, Calif.) RNeasy kits, following manufacturer's protocols, to a final concentration of 50 ng/μl. Single stranded cDNA was then synthesized by reverse transcribing the RNA samples using random hexamers and 500 ng of total RNA per reaction, following protocol 430-4965 of Applied Biosystems (Foster City, Calif.).

Primers for expression analysis using TaqMan assay (Applied Biosystems, Foster City, Calif.) were prepared according to the TaqMan protocols, and the following criteria: a) primer pairs were designed to span introns to eliminate genomic contamination, and b) each primer pair produced only one product. Expression analysis was performed using a 7900HT instrument.

Taqman reactions were carried out following manufacturer's protocols, in 25 μl total volume for 96-well plates and 10 μl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Number of pairs of tumor samples and matched normal tissue from the same patient are shown for each tumor type. Percentage of the samples with at least two-fold overexpression for each tumor type is provided. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

| ROR GI# | 19743899 | 19743906 | 21594879 |
|---|---|---|---|
| SEQ ID NO | 1 | 8 | 14 |
| Breast | 3% | 10% | 39% |
| # of Pairs | 30 | 30 | 36 |

TABLE 1-continued

| ROR GI# | 19743899 | 19743906 | 21594879 |
|---|---|---|---|
| Colon | 11% | 22% | 24% |
| # of Pairs | 36 | 36 | 41 |
| Head And Neck | 8% | 23% | 0% |
| # of Pairs | 13 | 13 | 13 |
| Kidney | 9% | 14% | 27% |
| # of Pairs | 22 | 22 | 22 |
| Liver | 0% | 40% | 20% |
| # of Pairs | 5 | 5 | 5 |
| Lung | 6% | 9% | 7% |
| # of Pairs | 35 | 35 | 41 |
| Lymphoma | 0% | 0% | 0% |
| # of Pairs | 3 | 3 | 3 |
| Ovary | 5% | 22% | 63% |
| # of Pairs | 19 | 18 | 19 |
| Pancreas | 33% | 56% | 33% |
| # of Pairs | 9 | 9 | 9 |
| Prostate | 7% | 7% | 14% |
| # of Pairs | 15 | 15 | 22 |
| Skin | 0% | 0% | 0% |
| # of Pairs | 7 | 7 | 7 |
| Stomach | 9% | 18% | 0% |
| # of Pairs | 11 | 11 | 11 |
| Testis | 0% | 0% | 12% |
| # of Pairs | 8 | 8 | 8 |
| Thyroid Gland | 7% | 0% | 14% |
| # of Pairs | 14 | 14 | 14 |
| Uterus | 0% | 5% | 43% |
| # of Pairs | 19 | 19 | 21 |

VI. ROR Functional Assays

RNAi experiments were carried out to knock down expression of ROR (SEQ ID NOs:1, 8, and 14) in various cell lines using small interfering RNAs (siRNA, Elbashir et al, supra).

Effect of ROR RNAi on cell proliferation and growth. BrdU, Cell Titer-Glo™, and MTS assays, as described above, were employed to study the effects of decreased ROR expression on cell proliferation. The results of these experiments indicated that: RNAi of SEQ ID NO:1 decreased proliferation in 231T (a variant of MDA 231) and MDA 231 breast cancer lines (with possible mitotic arrest in 231T cells), and A549 and LX1 lung cancer lines; RNAi of SEQ ID NO:8 decreased proliferation in LX1 lung cancer line and MCF7 breast cancer line; RNAi of SEQ ID NO:14 decreased proliferation in 231T, MDA231 and MCF7 breast cancer lines, LX1 and A549 lung cancer lines, and SW480 and HCT116 colon cancer lines.

Standard colony growth assays, as described above, were employed to study the effects of decreased ROR expression on cell growth. RNAi of SEQ ID NO:1 caused inhibition of cell growth in A549, LX1, and MDA 231 cells. RNAi of SEQ ID NO:8 caused inhibition of cell growth in A549, LX1, and MDA 231 cells. RNAi of SEQ ID NO:14 did not have an affect on cell growth.

Effect of ROR RNAi on apoptosis. Nucleosome ELISA apoptosis assay, as described above, was employed to study the effects of decreased ROR expression on apoptosis. RNAi of SEQ ID NO:1 increased apoptosis in LX1 and A549 cells; RNAi of SEQ ID NO:8 increased apoptosis in LX1 cells; and RNAi of ROR SEQ ID NO:14 increased apoptosis in LX1 and A549 cells.

ROR overexpression analysis. ROR sequences were overexpressed and tested in colony growth assays as described above. Overexpression of SEQ ID NO:8 had no morphological effects on cells, and moderate effects on colony growth. Overexpression of SEQ ID NO:14 had no morphological effects on cells, and moderate effects on colony growth. Effects of overexpression of SEQ ID NO:14 on expression of various transcription factors was also studied. Overexpression SEQ ID NO:14 caused an increased expression of the following transcription factors: SRE, AP1, ETS1, RARa (DR5) and ER.

What is claimed is:

1. A method of identifying a p21 pathway modulating agent, said method comprising the steps of:

(a) providing a first assay system comprising a Retinoic Acid Receptor Related Orphan Receptor (ROR) nucleic acid, wherein the nucleic acid is selected from the group consisting of SEQ ID NOs: 1-15, a nucleic acid encoding the polypeptide of SEQ ID NO: 16, 17, or 18, and a nucleic acid encoding amino acids 104-179 of SEQ ID NO: 16, amino acids 361-544 of SEQ ID NO: 16, amino acids 8-83 of SEQ ID NO: 17, amino acids 267-450 of SEQ ID NO: 17, amino acids 29-104 of SEQ ID NO: 18, or amino acids 325-506 of SEQ ID NO: 18;

(b) contacting the first assay system with a test agent that modulates the expression of the ROR nucleic acid of step (a);

(c) identifying the test agent as a p21 pathway modulating agent by detecting a change in the activity of the first assay system in the presence or absence of the test agent of step (b);

(d) providing a second assay system comprising cultured cells expressing ROR, wherein the second assay is capable of detecting a change in the p21 pathway;

(e) contacting the second assay system with the test agent of (b); and (f) confirming the test agent as a p21 pathway modulating agent by detecting a change in the second assay system in the presence or absence of the test agent.

2. The method of claim 1, wherein the first assay system comprises cultured cells.

3. The method of claim 2, wherein the cultured cells additionally have defective p21 expression or activity.

4. The method of claim 1, wherein the test agent is a nucleic acid modulator.

5. The method of claim 1, wherein the second assay system comprises an apoptosis assay, a cell proliferation assay, an angiogenesis assay, or a hypoxic induction assay.

6. The method of claim 1, wherein the first assay system includes an expression assay and the test agent is a nucleic acid modulator.

7. The method of claim 4, wherein the nucleic acid modulator is an antisense oligomer.

8. The method of claim 4, wherein the nucleic acid modulator is a phosphothioate morpholino oligomer (PMO).

9. The method of claim 4, wherein the nucleic acid modulator is a RNA inhibitor.

10. The method of claim 1, wherein the ROR nucleic acid is selected from the group consisting of SEQ ID NOs: 1, 8, and 14.

11. The method of claim 4, wherein the nucleic acid modulator binds to a ROR nucleic acid selected from the group consisting of SEQ ID NOs: 1-15.

12. The method of claim 4, wherein the nucleic acid modulator binds to a ROR nucleic acid that encodes amino acids 104-179 of SEQ ID NO: 16, amino acids 361-544 of SEQ ID NO: 16, amino acids 8-83 of SEQ ID NO: 17, amino acids 267-450 of SEQ ID NO: 17, amino acids 29-104 of SEQ ID NO: 18, or amino acids 325-506 of SEQ ID NO: 18.

13. The method of claim 9, wherein the RNA inhibitor is an siRNA molecule targeted to a ROR polynucleotide.

14. The method of claim 1, wherein the cultured cells in the second assay system additionally have defective p21 expression or activity.

15. The method of claim 1, wherein the second assay system comprises cells defective in p21 pathway function and the change detected in the second assay system is a phenotypic change that indicates that the p21 pathway function is restored.

* * * * *

SEQUENCE LISTING

```
<160> NUMBER OF SEQ ID NOS: 18

<210> SEQ ID NO 1
<211> LENGTH: 1996
<212> TYPE: DNA
<213> ORGANISM: Homo sapiens

<400> SEQUENCE: 1

gcagattcac agggcctctg agcattatcc cccatactcc tccccatcat tctccaccca      60

gctgttggag ccatctgtct gatcaccttg gactccatag tacactgggg caaagcacag     120

ccccagtttc tggaggcaga tgggtaacca ggaaaaggca tgaatgaggg ggccccagga     180

gacagtgact tagagactga ggcaagagtg ccgtggtcaa tcatgggtca ttgtcttcga     240

actggacagg ccagaatgtc tgccacaccc acacctgcag gtgaaggagc cagaagctct     300

tcaacctgta gctccctgag caggctgttc tggtctcaac ttgagcacat aaactgggat     360

ggagccacag ccaagaactt tattaattta agggagttct tctcttttct gctccctgca     420

ttgagaaaag ctcaaattga aattattcca tgcaagatct gtggagacaa atcatcagga     480

atccattatg gtgtcattac atgtgaaggc tgcaagggct ttttcaggag aagtcagcaa     540

agcaatgcca cctactcctg tcctcgtcag aagaactgtt tgattgatcg aaccagtaga     600

aaccgctgcc aacactgtcg attacagaaa tgccttgccg tagggatgtc tcgagatgct     660

gtaaaatttg gccgaatgtc aaaaaagcag agagacagct tgtatgcaga agtacagaaa     720
```

caccggatgc agcagcagca gcgcgaccac cagcagcagc ctggagaggc tgagccgctg 780
acgcccacct acaacatctc ggccaacggg ctgacggaac ttcacgacga cctcagtaac 840
tacattgacg ggcacacccc tgaggggagt aaggcagact ccgccgtcag cagcttctac 900
ctggacatac agccttcccc agaccagtca ggtcttgata tcaatggaat caaaccagaa 960
ccaatatgtg actacacacc agcatcaggc ttctttccct actgttcgtt caccaacggc 1020
gagacttccc caactgtgtc catggcagaa ttagaacacc ttgcacagaa tatatctaaa 1080
tcgcatctgg aaacctgcca atacttgaga gaagagctcc agcagataac gtggcagacc 1140
tttttacagg aagaaattga gaactatcaa aacaagcagc gggaggtgat gtggcaattg 1200
tgtgccatca aaattacaga agctatacag tatgtggtgg agtttgccaa acgcattgat 1260
ggatttatgg aactgtgtca aaatgatcaa attgtgcttc taaaagcagg ttctctagag 1320
gtggtgttta tcagaatgtg ccgtgccttt gactctcaga acaacaccgt gtactttgat 1380
gggaagtatg ccagccccga cgtcttcaaa tccttaggtt gtgaagactt tattagcttt 1440
gtgtttgaat ttggaaagag tttatgttct atgcacctga ctgaagatga aattgcatta 1500
ttttctgcat ttgtactgat gtcagcagat cgctcatggc tgcaagaaaa ggtaaaaatt 1560
gaaaaactgc aacagaaaat tcagctagct cttcaacacg tcctacagaa gaatcaccga 1620
gaagatggaa tactaacaaa gttaatatgc aaggtgtcta cattaagagc cttatgtgga 1680
cgacatacag aaaagctaat ggcatttaaa gcaatatacc cagacattgt gcgacttcat 1740
tttcctccat tatacaagga gttgttcact tcagaatttg agccagcaat gcaaattgat 1800
gggtaaatgt tatcacctaa gcacttctag aatgtctgaa gtacaaacat gaaaaacaaa 1860
caaaaaaatt aaccgagaca ctttatatgg ccctgcacag acctggagcg ccacacactg 1920
cacatctttt ggtgatcggg gtcaggcaaa ggaggggaaa caatgaaaac aaataaagtt 1980
gaacttgttt ttctca 1996

<210> SEQ ID NO 2
<211> LENGTH: 2020
<212> TYPE: DNA
<213> ORGANISM: Homo sapiens

<400> SEQUENCE: 2
gcagattcac agggcctctg agcattatcc cccatactcc tccccatcat tctccaccca 60
gctgttggag ccatctgtct gatcaccttg gactccatag tacactgggg caaagcacag 120
ccccagtttc tggaggcaga tgggtaacca ggaaaaggca tgaatgaggg ggccccagga 180
gacagtgact tagagactga ggcaagagtg ccgtggtcaa tcatgggtca ttgtcttcga 240
actggacagg ccagaatgtc tgccacaccc acacctgcag gtgaaggagc cagaagggat 300
gaactttttg ggattctcca aatactccat cagtgtatcc tgtcttcagg tgatgctttt 360
gttcttactg gcgtctgttg ttcctggagg cagaatggca agccaccata ttcacaaaag 420
gaagataagg aagtacaaac tggatacatg aatgctcaaa ttgaaattat tccatgcaag 480
atctgtggag acaaatcatc aggaatccat tatggtgtca ttacatgtga aggctgcaag 540
ggctttttca ggagaagtca gcaaagcaat gccacctact cctgtcctcg tcagaagaac 600
tgtttgattg atcgaaccag tagaaaccgc tgccaacact gtcgattaca gaaatgcctt 660
gccgtaggga tgtctcgaga tgctgtaaaa tttggccgaa tgtcaaaaaa gcagagagac 720
agcttgtatg cagaagtaca gaaacaccgg atgcagcagc agcagcgcga ccaccagcag 780
cagcctggag aggctgagcc gctgacgccc acctacaaca tctcggccaa cgggctgacg 840

-continued

```
gaacttcacg acgacctcag taactacatt gacgggcaca cccctgaggg gagtaaggca    900

gactccgccg tcagcagctt ctacctggac atacagcctt ccccagacca gtcaggtctt    960

gatatcaatg gaatcaaacc agaaccaata tgtgactaca caccagcatc aggcttcttt   1020

ccctactgtt cgttcaccaa cggcgagact tccccaactg tgtccatggc agaattagaa   1080

caccttgcac agaatatatc taaatcgcat ctggaaacct gccaatactt gagagaagag   1140

ctccagcaga taacgtggca gaccttttta caggaagaaa ttgagaacta tcaaaacaag   1200

cagcgggagg tgatgtggca attgtgtgcc atcaaaatta cagaagctat acagtatgtg   1260

gtggagtttg ccaaacgcat tgatggattt atggaactgt gtcaaaatga tcaaattgtg   1320

cttctaaaag caggttctct agaggtggtg tttatcagaa tgtgccgtgc ctttgactct   1380

cagaacaaca ccgtgtactt tgatgggaag tatgccagcc ccgacgtctt caaatcctta   1440

ggttgtgaag actttattag ctttgtgttt gaatttggaa agagtttatg ttctatgcac   1500

ctgactgaag atgaaattgc attattttct gcatttgtac tgatgtcagc agatcgctca   1560

tggctgcaag aaaaggtaaa aattgaaaaa ctgcaacaga aaattcagct agctcttcaa   1620

cacgtcctac agaagaatca ccgagaagat ggaatactaa caaagttaat atgcaaggtg   1680

tctacattaa gagccttatg tggacgacat acagaaaagc taatggcatt taaagcaata   1740

tacccagaca ttgtgcgact tcattttcct ccattataca aggagttgtt cacttcagaa   1800

tttgagccag caatgcaaat tgatgggtaa atgttatcac ctaagcactt ctagaatgtc   1860

tgaagtacaa acatgaaaaa caaacaaaaa aattaaccga gacactttat atggccctgc   1920

acagacctgg agcgccacac actgcacatc ttttggtgat cggggtcagg caaaggaggg   1980

gaaacaatga aaacaaataa agttgaactt gtttttctca                         2020
```

<210> SEQ ID NO 3
<211> LENGTH: 1847
<212> TYPE: DNA
<213> ORGANISM: Homo sapiens

<400> SEQUENCE: 3

```
ggtaccatag agttgctctg aaaacagaag atagagggag tctcggagct cgccatctcc     60

agcgatctct acattgggaa aaaacatgga gtcagctccg gcagcccccg accccgccgc    120

cagcgagcca ggcagcagcg gcgcggacgc ggccgccggc tccagggaga ccccgctgaa    180

ccaggaatcc gcccgcaaga gcgagccgcc tgccccggtg cgcagacaga gctattccag    240

caccagcaga ggtatctcag taacgaagaa gacacataca tctcaaattg aaattattcc    300

atgcaagatc tgtggagaca aatcatcagg aatccattat ggtgtcatta catgtgaagg    360

ctgcaagggc tttttcagga gaagtcagca aagcaatgcc acctactcct gtcctcgtca    420

gaagaactgt ttgattgatc gaaccagtag aaaccgctgc caacactgtc gattacagaa    480

atgccttgcc gtagggatgt ctcgagatgc tgtaaaattt ggccgaatgt caaaaaagca    540

gagagacagc ttgtatgcag aagtacagaa acaccggatg cagcagcagc agcgcgacca    600

ccagcagcag cctggagagg ctgagccgct gacgcccacc tacaacatct cggccaacgg    660

gctgacggaa cttcacgacg acctcagtaa ctacattgac gggcacaccc ctgaggggag    720

taaggcagac tccgccgtca gcagcttcta cctggacata cagccttccc cagaccagtc    780

aggtcttgat atcaatggaa tcaaaccaga accaatatgt gactacacac cagcatcagg    840

cttctttccc tactgttcgt tcaccaacgg cgagacttcc ccaactgtgt ccatggcaga    900

attagaacac cttgcacaga atatatctaa atcgcatctg gaaacctgcc aatacttgag    960
```

-continued

```
agaagagctc cagcagataa cgtggcagac ctttttacag gaagaaattg agaactatca   1020

aaacaagcag cgggaggtga tgtggcaatt gtgtgccatc aaaattacag aagctataca   1080

gtatgtggtg gagtttgcca aacgcattga tggatttatg gaactgtgtc aaaatgatca   1140

aattgtgctt ctaaaagcag gttctctaga ggtggtgttt atcagaatgt gccgtgcctt   1200

tgactctcag aacaacaccg tgtactttga tgggaagtat gccagccccg acgtcttcaa   1260

atccttaggt tgtgaagact ttattagctt tgtgtttgaa tttggaaaga gtttatgttc   1320

tatgcacctg actgaagatg aaattgcatt attttctgca tttgtactga tgtcagcaga   1380

tcgctcatgg ctgcaagaaa aggtaaaaat tgaaaaactg caacagaaaa ttcagctagc   1440

tcttcaacac gtcctacaga agaatcaccg agaagatgga atactaacaa agttaatatg   1500

caaggtgtct acattaagag ccttatgtgg acgacataca gaaaagctaa tggcatttaa   1560

agcaatatac ccagacattg tgcgacttca ttttcctcca ttatacaagg agttgttcac   1620

ttcagaattt gagccagcaa tgcaaattga tgggtaaatg ttatcaccta agcacttcta   1680

gaatgtctga agtacaaaca tgaaaaacaa acaaaaaaat taaccgagac actttatatg   1740

gccctgcaca gacctggagc gccacacact gcacatcttt tggtgatcgg ggtcaggcaa   1800

aggaggggaa acaatgaaaa caaataaagt tgaacttgtt tttctca                 1847
```

<210> SEQ ID NO 4
<211> LENGTH: 1950
<212> TYPE: DNA
<213> ORGANISM: Homo sapiens

<400> SEQUENCE: 4

```
ccatctgtct gatcaccttg gactccatag tacactgggg caaagcacag ccccagtttc     60

tggaggcaga tgggtaacca ggaaaaggca tgaatgaggg ggccccagga gacagtgact    120

tagagactga ggcaagagtg ccgtggtcaa tcatgggtca ttgtcttcga actggacagg    180

ccagaatgtc tgccacaccc acacctgcag gtgaaggagc cagaagggat gaactttttg    240

ggattctcca aatactccat cagtgtatcc tgtcttcagg tgatgctttt gttcttactg    300

gcgtctgttg ttcctggagg cagaatggca agccaccata ttcacaaaag gaagataagg    360

aagtacaaac tggatacatg aatgctcaaa ttgaaattat tccatgcaag atctgtggag    420

acaaatcatc aggaatccat tatggtgtca ttacatgtga aggctgcaag ggctttttca    480

ggagaagtca gcaaagcaat gccacctact cctgtcctcg tcagaagaac tgtttgattg    540

atcgaaccag tagaaaccgc tgccaacact gtcgattaca gaaatgcctt gccgtaggga    600

tgtctcgaga tgctgtaaaa tttggccgaa tgtcaaaaaa gcagagagac agcttgtatg    660

cagaagtaca gaaacaccgg atgcagcagc agcagcgcga ccaccagcag cagcctggag    720

aggctgagcc gctgacgccc acctacaaca tctcggccaa cgggctgacg gaacttcacg    780

acgacctcag taactacatt gacgggcaca cccctgaggg gagtaaggca gactccgccg    840

tcagcagctt ctacctggac atacagcctt ccccagacca gtcaggtctt gatatcaatg    900

gaatcaaacc agaaccaata tgtgactaca caccagcatc aggcttcttt ccctactgtt    960

cgttcaccaa cggcgagact tccccaactg tgtccatggc agaattagaa caccttgcac   1020

agaatatatc taaatcgcat ctggaaacct gccaatactt gagagaagag ctccagcaga   1080

taacgtggca gaccttttta caggaagaaa ttgagaacta tcaaaacaag cagcgggagg   1140

tgatgtggca attgtgtgcc atcaaaatta cagaagctat acagtatgtg gtggagtttg   1200

ccaaacgcat tgatggattt atggaactgt gtcaaaatga tcaaattgtg cttctaaaag   1260
```

-continued

```
caggttctct agaggtggtg tttatcagaa tgtgccgtgc ctttgactct cagaacaaca   1320

ccgtgtactt tgatgggaag tatgccagcc ccgacgtctt caaatcctta ggttgtgaag   1380

actttattag ctttgtgttt gaatttggaa agagtttatg ttctatgcac ctgactgaag   1440

atgaaattgc attattttct gcatttgtac tgatgtcagc agatcgctca tggctgcaag   1500

aaaaggtaaa aattgaaaaa ctgcaacaga aaattcagct agctcttcaa cacgtcctac   1560

agaagaatca ccgagaagat ggaatactaa caaagttaat atgcaaggtg tctacattaa   1620

gagccttatg tggacgacat acagaaaagc taatggcatt taaagcaata tacccagaca   1680

ttgtgcgact tcattttcct ccattataca aggagttgtt cacttcagaa tttgagccag   1740

caatgcaaat tgatgggtaa atgttatcac ctaagcactt ctagaatgtc tgaagtacaa   1800

acatgaaaaa caaacaaaaa aattaaccga gacactttat atggccctgc acagacctgg   1860

agcgccacac actgcacatc ttttggtgat cggggtcagg caaaggaggg gaaacaatga   1920

aaacaaataa agttgaactt gtttttctca                                    1950
```

<210> SEQ ID NO 5
<211> LENGTH: 1816
<212> TYPE: DNA
<213> ORGANISM: Homo sapiens

<400> SEQUENCE: 5

```
ggcacgaggg aaaaaacatg gagtcagctc cggcagcccc cgaccccgcc gccagcgagc     60

caggcagcag cggcgcggac gcggccgccg gctccaggga gaccccgctg aaccaggaat    120

ccgcccgcaa gagcgagccg cctgccccgg tgcgcagaca gagctattcc agcaccagca    180

gaggtatctc agtaacgaag aagacacata catctcaaat tgaaattatt ccatgcaaga    240

tctgtggaga caaatcatca ggaatccatt atggtgtcat tacatgtgaa ggctgcaagg    300

gctttttcag gagaagtcag caaagcaatg ccacctactc ctgtcctcgt cagaagaact    360

gtttgattga tcgaaccagt agaaaccgct gccaacactg tcgattacag aaatgccttg    420

ccgtagggat gtctcgagat gctgtaaaat ttggccgaat gtcaaaaaag cagagagaca    480

gcttgtatgc agaagtacag aaacaccgga tgcagcagca gcagcgcgac caccagcagc    540

agcctggaga ggctgagccg ctgacgccca cctacaacat ctcggccaac gggctgacgg    600

aacttcacga cgacctcagt aactacattg acgggcacac ccctgagggg agtaaggcag    660

actccgccgt cagcagcttc tacctggaca tacagccttc cccagaccag tcaggtcttg    720

atatcaatgg aatcaaacca gaaccaatat gtgactacac accagcatca ggcttctttc    780

cctactgttc gttcaccaac ggcgagactt ccccaactgt gtccatggca gaattagaac    840

accttgcaca gaatatatct aaatcgcatc tggaaacctg ccaatacttg agagaagagc    900

tccagcagat aacgtggcag accttttac aggaagaaat tgagaactat caaaacaagc     960

agcgggaggt gatgtggcaa ttgtgtgcca tcaaaattac agaagctata cagtatgtgg   1020

tggagtttgc caaacgcatt gatggattta tggaactgtg tcaaaatgat caaattgtgc   1080

ttctaaaagc aggttctcta gaggtggtgt ttatcagaat gtgccgtgcc tttgactctc   1140

agaacaacac cgtgtacttt gatgggaagt atgccagccc cgacgtcttc aaatccttag   1200

gttgtgaaga ctttattagc tttgtgtttg aatttggaaa gagtttatgt tctatgcacc   1260

tgactgaaga tgaaattgca ttattttctg catttgtact gatgtcagca gatcgctcat   1320

ggctgcaaga aaaggtaaaa attgaaaaac tgcaacagaa aattcagcta gctcttcaac   1380

acgtcctaca gaagaatcac cgagaagatg gaatactaac aaagttaata tgcaaggtgt   1440
```

ctacattaag agccttatgt ggacgacata cagaaaagct aatggcattt aaagcaatat 1500
acccagacat tgtgcgactt cattttcctc cattatacaa ggagttgttc acttcagaat 1560
ttgagccagc aatgcaaatt gatgggtaaa tgttatcacc taagcacttc tagaatgtct 1620
gaagtacaaa catgaaaaac aaacaaaaaa attaaccgag acactttata tggccctgca 1680
cagacctgga gcgccacaca ctgcacatct tttggtgatc ggggtcaggc aaaggagggg 1740
aaacaatgaa aacaaataaa agttgaactt gtttttctca tgaaaaaaaa aaaaaaaaaa 1800
aaaaaaaaaa aaaaaa 1816

<210> SEQ ID NO 6
<211> LENGTH: 1473
<212> TYPE: DNA
<213> ORGANISM: Homo sapiens

<400> SEQUENCE: 6
cgctctccgc accgcgctta aatgatgtat tttgtgatcg cagagatgaa agctcaaatt 60
gagattattc catgcaagat ctgtggagac aaatcatcag gaatccatta tggtgtcatt 120
acatgtgaag gctgcaaggg ctttttcagg agaagtcagc aaagcaatgc cacctactcc 180
tgtcctcgtc agaagaactg tttgattgat cgaaccagta gaaaccgctg ccaacactgt 240
cgattacaga aatgccttgc cgtagggatg tctcgagatg ctgtaaaatt tggccgaatg 300
tcaaaaaagc agagagacag cttgtatgca gaagtacaga aacaccggat gcagcagcag 360
cagcgcgacc accagcagca gcctggagag gctgagccgc tgacgcccac ctacaacatc 420
tcggccaacg ggctgacgga acttcacgac gacctcagta actacattga cgggcacacc 480
cctgagggga gtaaggcaga ctccgccgtc agcagcttct acctggacat acagccttcc 540
ccagaccagt caggtcttga tatcaatgga atcaaaccag aaccaatatg tgactacaca 600
ccagcatcag gcttctttcc ctactgttcg ttcaccaacg gcgagacttc cccaactgtg 660
tccatggcag aattagaaca ccttgcacag aatatatcta aatcgcatct ggaaacctgc 720
caatacttga gagaagagct ccagcagata acgtggcaga cctttttaca ggaagaaatt 780
gagaactatc aaaacaagca gcgggaggtg atgtggcaat tgtgtgccat caaaattaca 840
gaagctatac agtatgtggt ggagtttgcc aaacgcatcg atggatttat ggaactgtgt 900
caaaatgatc aaattgtgct tctaaaagca ggttctctag aggtggtgtt tatcagagtg 960
tgccgtgcct ttgactctca gaacaacacc gtgtactttg atgggaagta tgccagcccc 1020
gacgtcttca aatccttagg ttgtgaagac tttattagct ttgtgtttga atttggaaag 1080
agtttatgtt ctatgcacct gactgaagat gaaattgcat tattttctgc atttgtactg 1140
atgtcagcag atcgctcatg gctgcaagaa aaggtaaaaa ttgaaaaact gcaacagaaa 1200
attcagctag ctcttcaaca cgtcctacag aagaatcacc gagaagatgg aatgctaaca 1260
aagttaatat gcaaggtgtc tacattaaga gccttatgtg gacgacatac agaaaagcta 1320
atggcattta aagcaatata cccagacatt gtgcgacttc attttcctcc attatacaag 1380
gagttgttca cttcagaatt tgagccagca atgcaaattg atgggtaaat gttatcacct 1440
aagcacttct agaatgtctg aagtacaaac atg 1473

<210> SEQ ID NO 7
<211> LENGTH: 1687
<212> TYPE: DNA
<213> ORGANISM: Homo sapiens

<400> SEQUENCE: 7

-continued

```
tgtggctcgg gcggcggcgg cgcggcggcg gcagaggggg ctccggggtc ggaccatccg     60

ctctccctgc gctctccgca ccgcgcttaa atgatgtatt ttgtgatcgc agcgatgaaa    120

gctcaaattg aaattattcc atgcaagatc tgtggagaca aatcatcagg aatccattat    180

ggtgtcatta catgtgaagg ctgcaagggc tttttcagga gaagtcagca aagcaatgcc    240

acctactcct gtcctcgtca gaagaactgt ttgattgatc gaaccagtag aaaccgctgc    300

caacactgtc gattacagaa atgccttgcc gtagggatgt ctcgagatgc tgtaaaattt    360

ggccgaatgt caaaaaagca gagagacagc ttgtatgcag aagtacagaa acaccggatg    420

cagcagcagc agcgcgacca ccagcagcag cctggagagg ctgagccgct gacgcccacc    480

tacaacatct cggccaacgg gctgacggaa cttcacgacg acctcagtaa ctacattgac    540

gggcacaccc ctgaggggag taaggcagac tccgccgtca gcagcttcta cctggacata    600

cagccttccc cagaccagtc aggtcttgat atcaatggaa tcaaaccaga accaatatgt    660

gactacacac cagcatcagg cttctttccc tactgttcgt tcaccaacgg cgagacttcc    720

ccaactgtgt ccatggcaga attagaacac cttgcacaga atatatctaa atcgcatctg    780

gaaacctgcc aatacttgag agaagagctc cagcagataa cgtggcagac ctttttacag    840

gaagaaattg agaactatca aaacaagcag cgggaggtga tgtggcaatt gtgtgccatc    900

aaaattacag aagctataca gtatgtggtg gagtttgcca aacgcattga tggatttatg    960

gaactgtgtc aaaatgatca aattgtgctt ctaaaagcag gttctctaga ggtggtgttt   1020

atcagaatgt gccgtgcctt tgactctcag aacaacaccg tgtactttga tgggaagtat   1080

gccagccccg acgtcttcaa atccttaggt tgtgaagact ttattagctt tgtgtttgaa   1140

tttggaaaga gtttatgttc tatgcacctg actgaagatg aaattgcatt attttctgca   1200

tttgtactga tgtcagcaga tcgctcatgg ctgcaagaaa aggtaaaaat tgaaaaactg   1260

caacagaaaa ttcagctagc tcttcaacac gtcctacaga agaatcaccg agaagatgga   1320

atactaacaa agttaatatg caaggtgtct acattaagag ccttatgtgg acgacataca   1380

gaaaagctaa tggcatttaa agcaatatac ccagacattg tgcgacttca ttttcctcca   1440

ttatacaagg agttgttcac ttcagaattt gagccagcaa tgcaaattga tgggtaaatg   1500

ttatcaccta agcacttcta gaatgtctga agtacaaaca tgaaaaacaa acaaaaaaat   1560

taaccgagac actttatatg gccctgcaca gacctggagc gccacacact gcacatcttt   1620

tggtgatcgg ggtcaggcaa aggaggggaa acaatgaaaa caaataaagt tgaacttgtt   1680

tttctca                                                             1687
```

<210> SEQ ID NO 8
<211> LENGTH: 3243
<212> TYPE: DNA
<213> ORGANISM: Homo sapiens

<400> SEQUENCE: 8

```
gaacagtgaa aattcacatt gtggatccgc taacaggcac agatgtcatg tgaaaacgca     60

catgctctgc catccacacc gcctttcttt cttttctttc tgtttccttt tttcccctt    120

gttccttctc cctcttcttt gtaactaaca aaaccaccac caactcctcc tcctgctgct    180

gcccttcctc ctcctcctca gtccaagtga tcacaaaaga aatcttctga gccggaggcg    240

gtggcatttt ttaaaaagca agcacattgg agagaaagaa aaagaaaaac aaaaccaaaa    300

caaaacccag gcaccagaca gccagaacat ttttttttca cccttcctga aaacaaacaa    360

acaaacaaac aatcatcaaa acagtcacca ccaacatcaa aactgttaac atagcggcgg    420
```

-continued

```
cggcggcaaa cgtcaccctg cagccacggc gtccgcctaa agggatggtt ttctcggcag    480
agcagctctt cgccgaccac cttcttcact cgtgctgagc gggatttttg ggctctccgg    540
ggttcgggct gggagcagct tcatgactac gcggagcggg agagcggcca caccatgcga    600
gcacaaattg aagtgatacc atgcaaaatt tgtggcgata agtcctctgg gatccactac    660
ggagtcatca catgtgaagg ctgcaaggga ttctttagga ggagccagca gaacaatgct    720
tcttattcct gcccaaggca gagaaactgt ttaattgaca gaacgaacag aaaccgttgc    780
caacactgcc gactgcagaa gtgtcttgcc ctaggaatgt caagagatgc tgtgaagttt    840
gggaggatgt ccaagaagca aagggacagc ctgtatgctg aggtgcagaa gcaccagcag    900
cggctgcagg aacagcggca gcagcagagt ggggaggcag aagcccttgc cagggtgtac    960
agcagcagca ttagcaacgg cctgagcaac ctgaacaacg agaccagcgg cacttatgcc   1020
aacgggcacg tcattgacct gcccaagtct gagggttatt acaacgtcga ttccggtcag   1080
ccgtcccctg atcagtcagg acttgacatg actggaatca aacagataaa gcaagaacct   1140
atctatgacc tcacatccgt acccaacttg tttacctata gctctttcaa caatgggcag   1200
ttagcaccag ggataaccat gactgaaatc gaccgaattg cacagaacat cattaagtcc   1260
catttggaga catgtcaata caccatggaa gagctgcacc agctggcgtg gcagacccac   1320
acctatgaag aaattaaagc atatcaaagc aagtccaggg aagcactgtg gcaacaatgt   1380
gccatccaga tcactcacgc catccaatac gtggtggagt ttgcaaagcg gataacaggc   1440
ttcatggagc tctgtcaaaa tgatcaaatt ctacttctga agtcaggttg cttggaagtg   1500
gttttagtga gaatgtgccg tgccttcaac ccattaaaca acactgttct gtttgaagga   1560
aaatatggag gaatgcaaat gttcaaagcc ttaggttctg atgacctagt gaatgaagca   1620
tttgactttg caaagaattt gtgttccttg cagctgaccg aggaggagat cgctttgttc   1680
tcatctgctg ttctgatatc tccagaccga gcctggctta tagaaccaag gaaagtccag   1740
aagcttcagg aaaaaattta ttttgcactt caacatgtga ttcagaagaa tcacctggat   1800
gatgagacct tggcaaagtt aatagccaag ataccaacca tcacggcagt ttgcaacttg   1860
cacggggaga agctgcaggt atttaagcaa tctcatccag agatagtgaa tacactgttt   1920
cctccgttat acaaggagct ctttaatcct gactgtgcca ccggctgcaa atgaagggga   1980
caagagaact gtctcatagt catggaatgc atcaccatta agacaaaagc aatgtgttca   2040
tgaagactta agaaaaatgt cactactgca acattaggaa tgtcctgcac ttaatagaat   2100
tatttttcac cgctacagtt tgaagaatgt aaatatgcac ctgagtgggg ctcttttatt   2160
tgtttgtttg tttttgaaat gaccataaat atacaaatat aggacactgg gtgttatcct   2220
ttttttaatt ttattcgggt atgttttggg agacaactgt ttatagaatt ttattgtaga   2280
tatatacaag aaaagagcgg tactttacat gattactttt cctgttgatt gttcaaatat   2340
aatttaagaa aattccactt aataggctta cctatttcta tgtttttagg tagttgatgc   2400
atgtgtaaat ttgtagctgt cttggaaagt actgtgcatg tatgtaataa gtatataata   2460
tgtgagaata ttatatatga ctattactta tacatgcaca tgcactgtgg cttaaatacc   2520
atacctacta gcaatggagg ttcagtcagg ctctcttcta tgatttacct tctgtgttat   2580
atgttacctt tatgttagac aatcaggatt ttgttttccc agccagagtt ttcatctata   2640
gtcaatggca ggacggtacc aactcagagt taagtctaca aaggaataaa cataatgtgt   2700
ggcctctata tacaaactct atttctgtca atgacatcaa agccttgtca agatggttca   2760
tattgggaag gagacagtat tttaagccat tttcctgttt caagaattag gccacagata   2820
```

-continued

```
acattgcaag gtccaagact tttttgacca aacagtagat attttctatt tttcaccaga   2880

acacataaaa acactttttt tcttttggat ttctggttgt gaaacaagct tgatttcagt   2940

gcttattgtg tcttcaactg aaaaatacaa tctgtggatt atgactacca gcaatttttt   3000

tctaggaaag ttaaaagaat aaatcagaac ccagggcaac aatgccattt catgtaaaca   3060

ttttctctct caccatgttt tggcaagaaa aggtagaaag agaagaccca gagtgaagaa   3120

gtaattcttt atattccttt ctttaatgta tttgttagga aaagtggcaa taaaggggga   3180

ggcatattat aaaatgctat aatataaaaa tgtagcaaaa acttgacaga ctagaaaaaa   3240

aaa                                                                 3243
```

<210> SEQ ID NO 9
<211> LENGTH: 2026
<212> TYPE: DNA
<213> ORGANISM: Homo sapiens

<400> SEQUENCE: 9

```
gcagaacagt gaaaattcac attgtggatc cgctaacagg cacagatgtc atgtgaaaag     60

cacatgctct gccatccaca cgcctttctt tcttttcttt ctgtttcctt ttttcccccct   120

tgttccttct ccctcttctt tgtaactaac aaaaccacca ccaactcctc ctcctgctgc    180

tgcccttcct tcctcctcct cagtccaagt gatcacaaaa gaaatcttct gagccggagg    240

cggtggcatt ttttaaaaag caagcacatt ggagagaaag aaaaagaaaa acaaaaccaa    300

aacaaaaccc aggcaccaga cagccagaac attttttttc acccttcctg aaaacaaaca    360

aacaaacaaa caatcatcaa aacagtcacc accaacatca aaactgttaa catagcggcg    420

gcggcggcaa acgtcaccct gcagccacgg cgtccgctaa agggatggtt ttctcggcag    480

agcagctctt cgccgaccac cttcttcact cgtgctgagc gggatttttg ggctctccgg    540

ggttcgggct gggagcagct tcatgactac gcggagcggg agagcggcca caccatgcga    600

gcacaaattg aagtgatacc atgcaaaatt tgtggcgata agtcctctgg gatccactac    660

ggagtcatca catgtgaagg ctgcaaggga ttctttagga ggagccagca gaacaatgct    720

tcttattcct gcccaaggca gagaaactgt ttaattgaca gaacgaacag aaaccgttgc    780

caacactgcc gactgcagaa gtgtcttgcc ctaggaatgt caagagatgc tgtgaagttt    840

gggaggatgt ccaagaagca aagggacagc ctgtatgctg aggtgcagaa gcaccagcag    900

cggctgcagg aacagcggca ggagcagagt ggggaggcag aacgccttgc cagggtgtac    960

agcagcagca ttagcaacgg cctgagcaac ctgaacaacg agaccagcgg cacttatgcc   1020

aacggcagcg tcattgacct gcccaagtct gagggttatt acaacgtcgt ttccggtcag   1080

ccgtcccctg atcagtcagg acttgacatg actggaatca aacagataaa gcaagaacct   1140

atctatgacc tcacatccgt acccaacttg tttacctata gctctttcaa caatgggcag   1200

ttagcaccag ggataaccat gactgaaatc gaccgaattg cacagaacat cattaagtcc   1260

catttggaga catgtcaata caccatggaa gagctgcacc agctggcgtg gcagacccac   1320

acctatgaag aaattaaagc atatcaaagc aagtccaggg aagcactgtg gcaacaatgt   1380

gccatccaga tcactcacgc catccaatac gtggtggagt ttgcaaagcg gataacaggc   1440

ttcatggagc tctgtcaaaa tgatcaaatt ctacttctga agtcaggttg cttggaagtg   1500

gttttagtga gaatgtgccg tgccttcaac ccattaaaca acactgttct gtttgaagga   1560

aaatatggag gaatgcaaat gttcaaagcc ttaggttctg atgacctagt gaatgaagca   1620

tttgactttg caaagaattt gtgttccttg cagctgaccg aggaggagat cgctttgttc   1680
```

-continued

```
tcatctgctg ttctgatatc tccagaccga gcctggctta tagaaccaag gaaagtccag   1740

aagcttcagg aaaaaattta ttttgcactt caacatgtga ttcagaagaa tcacctggat   1800

gatgagacct tggcaaagtt aatagccaag ataccaacca tcacggcagt ttgcaacttg   1860

cacggggaga agctgcaggt atttaagcaa tctcatccag agatagtgaa tacactgttt   1920

cctccgttat acaaggagct ctttaatcct gactgtgcca ccgcgtgcaa atgaagggga   1980

caagagaact gtctcatagt catggaatgc atcaccatta agacaa                  2026


<210> SEQ ID NO 10
<211> LENGTH: 3586
<212> TYPE: DNA
<213> ORGANISM: Homo sapiens

<400> SEQUENCE: 10

ctttctctct cgctgctccc ttcctccctg taactgaaca gtgaaaattc acattgtgga     60

tccgctaaca ggcacagatg tcatgtgaaa acgcacatgc tctgccatcc acaccgcctt    120

tctttctttt ctttctgttt cctttttttcc cccttgttcc ttctccctct tctttgtaac    180

taacaaaacc accaccaact cctcctcctg ctgctgccct tcctcctcct cctcagtcca    240

agtgatcaca aaagaaatct tctgagccgg aggcggtggc attttttaaa aagcaagcac    300

attggagaga aagaaaaaga aaaacaaaac caaaacaaaa cccaggcacc agacagccag    360

aacatttttt tttcaccctt cctgaaaaca aacaaacaaa caaacaatca tcaaaacagt    420

caccaccaac atcaaaactg ttaacatagc ggcggcggcg gcaaacgtca ccctgcagcc    480

acggcgtccg cctaaaggga tggttttctc ggcagagcag ctcttcgccg accaccttct    540

tcactcgtgc tgagcgggat ttttggctc tccggggttc gggctgggag cagcttcatg    600

actacgcgga gcgggagagc ggccacacca tgcgagcaca aattgaagtg ataccatgca    660

aaatttgtgg cgataagtcc tctgggatcc actacggagt catcacatgt gaaggctgca    720

agggattctt taggaggagc cagcagaaca atgcttctta ttcctgccca aggcagagaa    780

actgtttaat tgacagaacg aacagaaacc gttgccaaca ctgccgactg cagaagtgtc    840

ttgccctagg aatgtcaaga gatgctgtga agtttgggag aatgtccaag aagcaaaggg    900

acagcctgta tgctgaggtg cagaagcacc agcagcggct gcaggaacag cggcagcagc    960

agagtgggga ggcagaagcc cttgccaggg tgtacagcag cagcattagc aacggcctga   1020

gcaacctgaa caacgagacc agcggcactt atgccaacgg gcacgtcatt gacctgccca   1080

agtctgaggg ttattacaac gtcgattccg gtcagccgtc ccctgatcag tcaggacttg   1140

acatgactgg aatcaaacag ataaagcaag aacctatcta tgacctcaca tccgtaccca   1200

acttgtttac ctatagctct ttcaacaatg ggcagttagc accagggata accatgactg   1260

aaatcgaccg aattgcacag aacatcatta agtcccattt ggagacatgt caatacacca   1320

tggaagagct gcaccagctg gcgtggcaga cccacaccta tgaagaaatt aaagcatatc   1380

aaagcaagtc cagggaagca ctgtggcaac aatgtgccat ccagatcact cacgccatcc   1440

aatacgtggt ggagtttgca aagcggataa caggcttcat ggagctctgt caaaatgatc   1500

aaattctact tctgaagtca ggttgcttgg aagtggtttt agtgagaatg tgccgtgcct   1560

tcaacccatt aaacaacact gttctgtttg aaggaaaata tggaggaatg caaatgttca   1620

aagccttagg ttctgatgac ctagtgaatg aagcatttga ctttgcaaag aatttgtgtt   1680

ccttgcagct gaccgaggag gagatcgctt tgttctcatc tgctgttctg atatctccag   1740

accgagcctg gcttatagaa ccaaggaaag tccagaagct tcaggaaaaa atttattttg   1800
```

cacttcaaca tgtgattcag aagaatcacc tggatgatga gaccttggca aagttaatag 1860
ccaagatacc aaccatcacg gcagtttgca acttgcacgg ggagaagctg caggtattta 1920
agcaatctca tccagagata gtgaatacac tgtttcctcc gttatacaag gagctcttta 1980
atcctgactg tgccaccggc tgcaaatgaa ggggacaaga gaactgtctc atagtcatgg 2040
aatgcatcac cattaagaca aaagcaatgt gttcatgaag acttaagaaa aatgtcacta 2100
ctgcaacatt aggaatgtcc tgcacttaat agaattattt ttcaccgcta cagtttgaag 2160
aatgtaaata tgcacctgag tggggctctt ttatttgttt gtttgttttt gaaatgacca 2220
taaatataca aatataggac actgggtgtt atcctttttt taattttatt cgggtatgtt 2280
ttgggagaca actgtttata gaattttatt gtagatatat acaagaaaag agcggtactt 2340
tacatgatta cttttcctgt tgattgttca aatataattt aagaaaattc cacttaatag 2400
gcttacctat ttctatgttt ttaggtagtt gatgcatgtg taaatttgta gctgtcttgg 2460
aaagtactgt gcatgtatgt aataagtata taatatgtga gaatattata tatgactatt 2520
acttatacat gcacatgcac tgtggcttaa ataccatacc tactagcaat ggaggttcag 2580
tcaggctctc ttctatgatt taccttctgt gttatatgtt acctttatgt tagacaatca 2640
ggattttgtt ttcccagcca gagttttcat ctatagtcaa tggcaggacg gtaccaactc 2700
agagttaagt ctacaaagga ataaacataa tgtgtggcct ctatatacaa actctatttc 2760
tgtcaatgac atcaaagcct tgtcaagatg gttcatattg ggaaggagac agtattttaa 2820
gccattttcc tgtttcaaga attaggccac agataacatt gcaaggtcca agactttttt 2880
gaccaaacag tagatatttt ctatttttca ccagaacaca taaaaacact ttttttcttt 2940
tggatttctg gttgtgaaac aagcttgatt tcagtgctta ttgtgtcttc aactgaaaaa 3000
tacaatctgt ggattatgac taccagcaat ttttttctag gaaagttaaa agaataaatc 3060
agaacccagg gcaacaatgc catttcatgt aaacattttc tctctcacca tgttttggca 3120
agaaaaggta gaaagagaag acccagagtg aagaagtaat tctttatatt cctttcttta 3180
atgtatttgt taggaaaagt ggcaataaag ggggaggcat attataaaat gctataaatat 3240 aaaaatgtag caaaaacttg acagactaga aaaaaaaaga tctgtgttat tctagggaac 3300
taatgtaccc caaagccaaa actaattcct gtgaagttta cagttacatc atccatttac 3360
cctagaatta tttttttagc aacttttaga aataaagaat acaactgtga cattaggatc 3420
agagatttta gacttccttg tacaaattct cacttctcca cctgctcacc aatgaaatta 3480
atcataagaa aagcatatat tccaagaaat ttgttctgcc tgtgtcctgg aggcctatac 3540
ctctgttatt ttctgataca aaataaaact taaaaaaaaa aaaaaa 3586

<210> SEQ ID NO 11
<211> LENGTH: 1821
<212> TYPE: DNA
<213> ORGANISM: Homo sapiens

<400> SEQUENCE: 11
cccctgggcc ctgctccctg ccctcctggg cagccagggc agccaggacg gcaccaaggg 60
agctgcccca tggacagggc cccacagaga cagcaccgag cctcacggga gctgctggct 120
gcaaagaaga cccacacctc acaaattgaa gtgatccctt gcaaaatctg tggggacaag 180
tcgtctggga tccactacgg ggttatcacc tgtgaggggt gcaagggctt cttccgccgg 240
agccagcgct gtaacgcggc ctactcctgc acccgtcagc agaactgccc catcgaccgc 300
accagccgaa accgatgcca gcactgccgc ctgcagaaat gcctggcgct gggcatgtcc 360

-continued

```
cgagatgctg tcaagttcgg ccgcatgtcc aagaagcaga gggacagcct gcatgcagaa    420

gtgcagaaac agctgcagca gcggcaacag cagcaacagg aaccagtggt caagacccct    480

ccagcagggg cccaaggagc agataccctc acctacacct tggggctccc agacgggcag    540

ctgcccctgg gctcctcgcc tgacctgcct gaggcttctg cctgtccccc tggcctcctg    600

aaagcctcag gctctgggcc ctcatattcc aacaacttgg ccaaggcagg gctcaatggg    660

gcctcatgcc accttgaata cagccctgag cggggcaagg ctgagggcag agagagcttc    720

tatagcacag gcagccagct gacccctgac cgatgtggac ttcgttttga ggaacacagg    780

catcctgggc ttggggaact gggacagggc ccagacagct acggcagccc cagtttccgc    840

agcacaccgg aggcacccta tgcctccctg acagagatag agcacctggt gcagagcgtc    900

tgcaagtcct acagggagac atgccagctg cggctggagg acctgctgcg gcagcgctcc    960

aacatcttct cccgggagga agtgactggc taccagagga agtccatgtg ggagatgtgg   1020

gaacggtgtg cccaccacct caccgaggcc attcagtacg tggtggagtt cgccaagagg   1080

ctctcaggct ttatggagct ctgccagaat gaccagattg tgcttctcaa agcaggagca   1140

atggaagtgg tgctggttag gatgtgccgg gcctacaatg ctgacaaccg cacggtcttt   1200

tttgaaggca aatacggtgg catggagctg ttccgagcct tgggctgcag cgagctcatc   1260

agctccatct ttgacttctc ccactcccta agtgccttgc acttttccga ggatgagatt   1320

gccctctaca cagcccttgt tctcatcaat gcccatcggc cagggctcca agagaaaagg   1380

aaagtagaac agctgcagta caatctggag ctggcctttc atcatcatct ctgcaagact   1440

catcgccaaa gcatcctggc aaagctgcca cccaagggga agcttcggag cctgtgtagc   1500

cagcatgtgg aaaggctgca gatcttccag cacctccacc ccatcgtggt ccaagccgct   1560

ttccctccac tctacaagga gctcttcagc actgaaaccg agtcacctgt ggggctgtcc   1620

aagtgacctg gaagagggac tccttgcctc tccctatggc ctgctggccc acctccctgg   1680

accccgttcc accctcaccc ttttcctttc ccatgaaccc tggagggtgg tccccaccag   1740

ctctttggaa gtgagcagat gctgcggctg gctttctgtc agcaggccgg cctggcagtg   1800

ggacaatcgc cagagggtgg g                                             1821
```

<210> SEQ ID NO 12
<211> LENGTH: 3054
<212> TYPE: DNA
<213> ORGANISM: Homo sapiens

<400> SEQUENCE: 12

```
agagagctag gtgcagagct tcaggctgag gcgctgctga gagggcctcg ccccgcctct     60

gccgccagct gcaccccact cctggaccac cccctgctga gaaggacagg gagccaaggc    120

cggcagagcc aaggctcagt catgagaaca caaattgaag tgatcccttg caaaatctgt    180

ggggacaagt cgtctgggat ccactacggg gttatcacct gtgaggggtg caagggcttc    240

ttccgccgga gccagcgctg taacgcggcc tactcctgca cccgtcagca gaactgcccc    300

atcgaccgca ccagccgaaa ccgatgccag cactgccgcc tgcagaaatg cctggcgctg    360

ggcatgtccc gagatgctgt caagttcggc cgcatgtcca agaagcagag ggacagcctg    420

catgcagaag tgcagaaaca gctgcagcag cggcaacagc agcaacagga accagtggtc    480

aagacccctc cagcaggggc ccaaggagca gataccctca cctacacctt ggggctccca    540

gacgggcagc tgcccctggg ctcctcgcct gacctgcctg aggcttctgc ctgtccccct    600

ggcctcctga aagcctcagg ctctgggccc tcatattcca acaacttggc caaggcaggg    660
```

-continued

```
ctcaatgggg cctcatgcca ccttgaatac agccctgagc ggggcaaggc tgagggcaga    720
gagagcttct atagcacagg cagccagctg acccctgacc gatgtggact tcgttttgag    780
gaacacaggc atcctgggct tggggaactg ggacagggcc cagacagcta cggcagcccc    840
agtttccgca gcacaccgga ggcaccctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc   1080
gccaagaggc tctcaggctt tatggagctc tgccagaatg accagattgt gcttctcaaa   1140
gcaggagcaa tggaagtggt gctggttagg atgtgccggg cctacaatgc tgacaaccgc   1200
acggtctttt ttgaaggcaa atacggtggc atggagctgt tccgagcctt gggctgcagc   1260
gagctcatca gctccatctt tgacttctcc cactccctaa gtgccttgca cttttccgag   1320
gatgagattg ccctctacac agcccttgtt ctcatcaatg cccatcggcc agggctccaa   1380
gagaaaagga aagtagaaca gctgcagtac aatctggagc tggcctttca tcatcatctc   1440
tgcaagactc atcgccaaag catcctggca aagctgccac ccaaggggaa gcttcggagc   1500
ctgtgtagcc agcatgtgga aaggctgcag atcttccagc acctccaccc catcgtggtc   1560
caagccgctt tccctccact ctacaaggag ctcttcagca ctgaaaccga gtcacctgtg   1620
gggctgtcca agtgacctgg aagagggact ccttgcctct ccctatggcc tgctggccca   1680
cctccctgga ccccgttcca ccctcaccct tttcctttcc catgaaccct ggagggtggt   1740
ccccaccagc tctttggaag tgagcagatg ctgcggctgg ctttctgtca gcaggccggc   1800
ctggcagtgg gacaatcgcc agagggtggg gctggcagaa caccatctcc agcctcagct   1860
ttgacctgtc tcatttccca tattccttca cacccagctt ctggaaggca tggggtggct   1920
gggatttaag gacttctggg ggaccaagac atcctcaaga aaacaggggc atccagggct   1980
ccctggatga atagaatgca attcattcag aagctcagaa gctaagaata agcctttgaa   2040
atacctcatt gcatttccct ttgggcttcg gcttggggag atggatcaag ctcagagact   2100
ggcagtgaga gcccagaagg acctgtataa aatgaatctg gagctttaca ttttctgcct   2160
ctgccttcct cccagctcag caaggaagta tttgggcacc ctacccttta cctggggtct   2220
aaccaaaaat ggatgggatg aggatgagag gctggagata attgttttat gggatttggg   2280
tgtgggacta gggtacaatg aaggccaaga gcatctcaga catagagtta aaactcaaac   2340
ctcttatgtg cactttaaag atagacttta ggggctggca caaatctgat cagagacaca   2400
tatccataca caggtgaaac acatacagac tcaacagcaa tcatgcagtt ccagagacac   2460
atgaacctga cacaatctct cttatccttg aggccacagc ttggaggagc ctagaggcct   2520
caggggaaag tcccaatcct gagggaccct cccaaacatt tccatggtgc tccagtccac   2580
tgatcttggg tctggggtga tccaaatacc accccagctc cagctgtctt ctaccactag   2640
aagacccaag agaagcagaa gtcgctcgca ctggtcagtc ggaaggcaag atcagatcct   2700
ggaggacttt cctggcctgc ccgccagccc tgctcttgtt gtggagaagg aagcagatgt   2760
gatcacatca ccccgtcatt gggcaccgct gactccagca tggaggacac cagggagcag   2820
ggcctgggcc tgtttcccca gctgtgatct tgcccagaac ctctcttggc ttcataaaca   2880
gctgtgaacc ctcccctgaa ggattaacag caatgatggg cagtcgtgga gttggggggg   2940
ttgggggtgg gattgtgtcc tctaagggga cgggttcatc tgagtaaaca taaaccccaa   3000
cttgtgccat tctttataaa atgattttaa aggcaaaaaa aaaaaaaaaa aaaa         3054
```

-continued

<210> SEQ ID NO 13
<211> LENGTH: 1819
<212> TYPE: DNA
<213> ORGANISM: Homo sapiens

<400> SEQUENCE: 13

```
ccccctgggcc ctgctccctg ccctcctggg cagccagggc agccaggacg gcaccaaggg     60
agctgcccca tggacagggc cccacagaga cagcaccgag cctcacggga gctgctggct    120
gcaaagaaga cccacacctc acaaattgaa gtgatccctt gcaaaatctg tggggacaag    180
tcgtctggga tccactacgg ggttatcacc tgtgaggggt gcaagggctt cttccgccgg    240
agccagcgct gtaacgcggc ctactcctgc acccgtcagc agaactgccc catcgaccgc    300
accagccgaa accgatgcca gcactgccgc ctgcagaaat gcctggcgct ggggatgtcc    360
cgagatgctg tcaagttcgg ccgcatgtcc aagaagcaga gggacagcct gcatgcagaa    420
gtgcagaaac agctgcagca gcggcaacag cagcaacagg aaccagtggt caagacccct    480
ccagcagggg cccaaggagc agataccctc acctacacct tggggctccc agacgggcag    540
ctgcccctgg gctcctcgcc tgacctgcct gaggcttctg cctgtccccc tggcctcctg    600
aaagcctcag gctctgggcc ctcatattcc aacaacttgg ccaaggcagg gctcaatggg    660
gcctcatgcc accttgaata cagccctgag cggggcaagg ctgagggcag agagagcttc    720
tatagcacag gcagccagct gacccctgac cgatgtggac ttcgttttga ggaacacagg    780
catcctgggc ttggggaact gggacagggc ccagacagct acggcagccc cagtttccgc    840
agcacaccgg aggcacccta tgcctccctg acagagatag agcacctggt gcagagcgtc    900
tgcaagtcct acagggagac atgccagctg cggctggagg acctgctgcg gcagcgctcc    960
aacatcttct cccgggagga agtgactggc taccagagga agtccatgtg ggagatgtgg   1020
gaacggtgtg cccaccacct caccgaggcc attcagtacg tggtggagtt cgccaagagg   1080
ctctcaggct ttatggagct ctgccagaat gaccagattg tgcttctcaa agcaggagca   1140
atggaagtgg tgctggttag gatgtgccgg gcctacaatg ctgacaaccg cacggtcttt   1200
tttgaaggca aatacggtgg catggagctg ttccgagcct tgggctgcag cgagctcatc   1260
agctccatct ttgacttctc ccactcccta agtgccttgc acttttccga ggatgagatt   1320
gccctctaca cagcccttgt tctcatcaat gcccatcggc cagggctcca agagaaaagg   1380
aaagtagaac agctgcagta caatctggag ctggcctttc atcatcatct ctgcaagact   1440
catcgccaaa gcatcctggc aaagctgcca cccaagggga agcttcggag cctgtgtagc   1500
cagcatgtgg aaaggctgca gatcttccag cacctccacc ccatcgtggt ccaagccgct   1560
ttccctccac tctacaagga gctcttcagc actgaaaccg agtcacctgt gggctgtcca   1620
agtgacctgg aagagggact ccttgcctct ccctatggcc tgctggccac ctccctggac   1680
cccgttccac cctcaccctt ttcctttccc atgaaccctg gagggtggtc cccaccagct   1740
ctttggaagt gagcagatgc tgcggctggc tttctgtcag caggccggcc tggcagtggg   1800
acaatcgcca gagggtggg                                                 1819
```

<210> SEQ ID NO 14
<211> LENGTH: 2150
<212> TYPE: DNA
<213> ORGANISM: Homo sapiens

<400> SEQUENCE: 14

```
caggacggca ccaagggagc tgccccatgg acagggcccc acagagacag caccgagcct     60
```

-continued

```
cacgggagct gctggctgca aagaagaccc acacctcaca aattgaagtg atcccttgca    120

aaatctgtgg ggacaagtcg tctgggatcc actacggggt tatcacctgt gaggggtgca    180

agggcttctt ccgccggagc cagcgctgta acgcggccta ctcctgcacc cgtcagcaga    240

actgccccat cgaccgcacc agccgaaacc gatgccagca ctgccgcctg cagaaatgcc    300

tggcgctggg catgtcccga gatgctgtca agttcggccg catgtccaag aagcagaggg    360

acagcctgca tgcagaagtg cagaaacagc tgcagcagcg gcaacagcag caacaggaac    420

cagtggtcaa gacccctcca gcaggggccc aaggagcaga taccctcacc tacaccttgg    480

ggctcccaga cgggcagctg cccctgggct cctcgcctga cctgcctgag gcttctgcct    540

gtcccccctgg cctcctgaaa gcctcaggct ctgggccctc atattccaac aacttggcca    600

aggcagggct caatggggcc tcatgccacc ttgaatacag ccctgagcgg ggcaaggctg    660

agggcagaga gagcttctat agcacaggca gccagctgac ccctgaccga tgtggacttc    720

gttttgagga acacaggcat cctgggcttg gggaactggg acagggccca gacagctacg    780

gcagccccag tttccgcagc acaccggagg caccctatgc ctccctgaca gagatagagc    840

acctggtgca gagcgtctgc aagtcctaca gggagacatg ccagctgcgg ctggaggacc    900

tgctgcggca gcgctccaac atcttctccc gggaggaagt gactggctac cagaggaagt    960

ccatgtggga gatgtgggaa cggtgtgccc accacctcac cgaggccatt cagtacgtgg   1020

tggagttcgc caagaggctc tcaggcttta tggagctctg ccagaatgac cagattgtgc   1080

ttctcaaagc aggagcaatg gaagtggtgc tggttaggat gtgccgggcc tacaatgctg   1140

acaaccgcac ggtctttttt gaaggcaaat acggtggcat ggagctgttc cgagccttgg   1200

gctgcagcga gctcatcagc tccatctttg acttctccca ctccctaagt gccttgcact   1260

tttccgagga tgagattgcc ctctacacag cccttgttct catcaatgcc catcggccag   1320

ggctccaaga gaaaaggaaa gtagaacagc tgcagtacaa tctggagctg gcctttcatc   1380

atcatctctg caagactcat cgccaaagca tcctggcaaa gctgccaccc aaggggaagc   1440

ttcggagcct gtgtagccag catgtggaaa ggctgcagat cttccagcac ctccacccca   1500

tcgtggtcca agccgctttc cctccactct acaaggagct cttcagcact gaaaccgagt   1560

cacctgtggg gctgtccaag tgacctggaa gagggactcc ttgcctctcc ctatggcctg   1620

ctggcccacc tccctggacc ccgttccacc ctcacccttt tcctttccca tgaaccctgg   1680

agggtggtcc ccaccagctc tttggaagtg agcagatgct gcggctggct ttctgtcagc   1740

aggccggcct ggcagtggga caatcgccag agggtggggc tggcagaaca ccatctccag   1800

cctcagcttt gacctgtctc atttcccata ttccttcaca cccagcttct ggaaggcatg   1860

gggtggctgg gatttaagga cttctggggg accaagacat cctcaagaaa acaggggcat   1920

ccagggctcc ctggatgaat agaatgcaat tcattcagaa gctcagaagc taagaataag   1980

cctttgaaat acctcattgc atttcccttt gggcttcggc ttggggagat ggatcaagct   2040

cagagactgg cagtgagagc ccataaggac ctgtataaaa tgaatctgga gctttaaaaa   2100

aaaaaaaaaa aaaaaaaaaa aaaaaaaaaa aaaaaaaaaa aaaaaaaaaa              2150
```

<210> SEQ ID NO 15
<211> LENGTH: 2161
<212> TYPE: DNA
<213> ORGANISM: Homo sapiens

<400> SEQUENCE: 15

```
agaagcactg ggggagagag ctaggtgcag agcttcaggc tgaggcgctg ctgagagggc     60
```

-continued

```
ctcgccccgc ctctgccgcc agctgcaccc cactcctgga ccaccccctg ctgagaagga    120

cagggagcca aggccggcag agccaaggct cagtcatgag aacacaaatt gaagtgatcc    180

cttgcaaaat ctgtggggac aagtcgtctg ggatccacta cggggttatc acctgtgagg    240

ggtgcaaggg cttcttccgc cggagccagc gctgtaacgc ggcctactcc tgcacccgtc    300

agcagaactg ccccatcgac cgcaccagcc gaaaccgatg ccagcactgc cgcctgcaga    360

aatgcctggc gctgggcatg tcccgagatg ctgtcaagtt cggccgcatg tccaagaagc    420

agagggacag cctgcatgca gaagtgcaga aacagctgca gcagcggcaa cagcagcaac    480

aggaaccagt ggtcaagacc cctccagcag ggggcccaagg agcagatacc ctcacctaca    540

ccttggggct cccagacggg cagctgcccc tgggctcctc gcctgacctg cctgaggctt    600

ctgcctgtcc ccctggcctc ctgaaagcct caggctctgg gccctcatat tccaacaact    660

tggccaaggc agggctcaat ggggcctcat gccaccttga atacagccct gagcggggca    720

aggctgaggg cagagagagc ttctatagca caggcagcca gctgacccct gaccgatgtg    780

gacttcgttt tgaggaacac aggcatcctg ggcttgggga actgggacag ggcccagaca    840

gctacggcag ccccagtttc cgcagcacac cggaggcacc ctatgcctcc ctgacagaga    900

tagagcacct ggtgcagagc gtctgcaagt cctacaggga gacatgccag ctgcggctgg    960

aggacctgct gcggcagcgc tccaacatct tctcccggga ggaagtgact ggctaccaga   1020

ggaagtccat gtgggagatg tgggaacggt gtgcccacca cctcaccgag gccattcagt   1080

acgtggtgga gttcgccaag aggctctcag gctttatgga gctctgccag aatgaccaga   1140

ttgtgcttct caaagcagga gcaatggaag tggtgctggt taggatgtgc cgggcctaca   1200

atgctgacaa ccgcacggtc ttttttgaag gcaaatacgg tggcatggag ctgttccgag   1260

ccttgggctg cagcgagctc atcagctcca tctttgactt ctcccactcc ctaagtgcct   1320

tgcacttttc cgaggatgag attgccctct acacagccct tgttctcatc aatgcccatc   1380

ggccagggct ccaagagaaa aggaaagtag aacagctgca gtacaatctg gagctggcct   1440

ttcatcatca tctctgcaag actcatcgcc aaagcatcct ggcaaagctg ccacccaagg   1500

ggaagcttcg gagcctgtgt agccagcatg tggaaaggct gcagatcttc cagcacctcc   1560

accccatcgt ggcccaagcc gctttccctc cactctacaa ggagctcttc agcactgaaa   1620

ccgagtcacc tgtggggctg tccaagtgac ctggaagagg gactccttgc ctctccctat   1680

ggcctgctgg cccacctccc tggaccccgt tccaccctca ccctttttcct ttcccatgaa   1740

ccctggaggg tggtccccac cagctctttg gaagtgagca gatgctgcgg ctggctttct   1800

gtcagcaggc cggcctggca gtgggacaat cgccagaggg tggggctggc agaacaccat   1860

ctccagcctc agctttgacc tgtctcattt cccatattcc ttcacaccca gcttctggaa   1920

ggcatggggt ggctgggatt taaggacttc tgggggacca agacatcctc aagaaaacag   1980

gggcatccag ggctccctgg atgaatagaa tgcaattcat tcagaagctc agaagctaag   2040

aataagcctt tgaaatacct cattgcattt ccctttgggc ttcggcttgg ggagatggat   2100

caagctcaga gactggcagt gagagcccag aaggacctgt ataaaatgaa tctggagctt   2160

t                                                                   2161
```

<210> SEQ ID NO 16
<211> LENGTH: 556
<212> TYPE: PRT
<213> ORGANISM: Homo sapiens

<400> SEQUENCE: 16

-continued

```
Met Asn Glu Gly Ala Pro Gly Asp Ser Asp Leu Glu Thr Glu Ala Arg
1               5                   10                  15

Val Pro Trp Ser Ile Met Gly His Cys Leu Arg Thr Gly Gln Ala Arg
            20                  25                  30

Met Ser Ala Thr Pro Thr Pro Ala Gly Glu Gly Ala Arg Arg Asp Glu
        35                  40                  45

Leu Phe Gly Ile Leu Gln Ile Leu His Gln Cys Ile Leu Ser Ser Gly
    50                  55                  60

Asp Ala Phe Val Leu Thr Gly Val Cys Cys Ser Trp Arg Gln Asn Gly
65                  70                  75                  80

Lys Pro Pro Tyr Ser Gln Lys Glu Asp Lys Glu Val Gln Thr Gly Tyr
                85                  90                  95

Met Asn Ala Gln Ile Glu Ile Ile Pro Cys Lys Ile Cys Gly Asp Lys
            100                 105                 110

Ser Ser Gly Ile His Tyr Gly Val Ile Thr Cys Glu Gly Cys Lys Gly
        115                 120                 125

Phe Phe Arg Arg Ser Gln Gln Ser Asn Ala Thr Tyr Ser Cys Pro Arg
    130                 135                 140

Gln Lys Asn Cys Leu Ile Asp Arg Thr Ser Arg Asn Arg Cys Gln His
145                 150                 155                 160

Cys Arg Leu Gln Lys Cys Leu Ala Val Gly Met Ser Arg Asp Ala Val
                165                 170                 175

Lys Phe Gly Arg Met Ser Lys Lys Gln Arg Asp Ser Leu Tyr Ala Glu
            180                 185                 190

Val Gln Lys His Arg Met Gln Gln Gln Gln Arg Asp His Gln Gln Gln
        195                 200                 205

Pro Gly Glu Ala Glu Pro Leu Thr Pro Thr Tyr Asn Ile Ser Ala Asn
    210                 215                 220

Gly Leu Thr Glu Leu His Asp Asp Leu Ser Asn Tyr Ile Asp Gly His
225                 230                 235                 240

Thr Pro Glu Gly Ser Lys Ala Asp Ser Ala Val Ser Ser Phe Tyr Leu
                245                 250                 255

Asp Ile Gln Pro Ser Pro Asp Gln Ser Gly Leu Asp Ile Asn Gly Ile
            260                 265                 270

Lys Pro Glu Pro Ile Cys Asp Tyr Thr Pro Ala Ser Gly Phe Phe Pro
        275                 280                 285

Tyr Cys Ser Phe Thr Asn Gly Glu Thr Ser Pro Thr Val Ser Met Ala
    290                 295                 300

Glu Leu Glu His Leu Ala Gln Asn Ile Ser Lys Ser His Leu Glu Thr
305                 310                 315                 320

Cys Gln Tyr Leu Arg Glu Glu Leu Gln Gln Ile Thr Trp Gln Thr Phe
                325                 330                 335

Leu Gln Glu Glu Ile Glu Asn Tyr Gln Asn Lys Gln Arg Glu Val Met
            340                 345                 350

Trp Gln Leu Cys Ala Ile Lys Ile Thr Glu Ala Ile Gln Tyr Val Val
        355                 360                 365

Glu Phe Ala Lys Arg Ile Asp Gly Phe Met Glu Leu Cys Gln Asn Asp
    370                 375                 380

Gln Ile Val Leu Leu Lys Ala Gly Ser Leu Glu Val Val Phe Ile Arg
385                 390                 395                 400

Met Cys Arg Ala Phe Asp Ser Gln Asn Asn Thr Val Tyr Phe Asp Gly
                405                 410                 415

Lys Tyr Ala Ser Pro Asp Val Phe Lys Ser Leu Gly Cys Glu Asp Phe
            420                 425                 430
```

```
Ile Ser Phe Val Phe Glu Phe Gly Lys Ser Leu Cys Ser Met His Leu
        435                 440                 445

Thr Glu Asp Glu Ile Ala Leu Phe Ser Ala Phe Val Leu Met Ser Ala
    450                 455                 460

Asp Arg Ser Trp Leu Gln Glu Lys Val Lys Ile Glu Lys Leu Gln Gln
465                 470                 475                 480

Lys Ile Gln Leu Ala Leu Gln His Val Leu Gln Lys Asn His Arg Glu
                485                 490                 495

Asp Gly Ile Leu Thr Lys Leu Ile Cys Lys Val Ser Thr Leu Arg Ala
            500                 505                 510

Leu Cys Gly Arg His Thr Glu Lys Leu Met Ala Phe Lys Ala Ile Tyr
        515                 520                 525

Pro Asp Ile Val Arg Leu His Phe Pro Pro Leu Tyr Lys Glu Leu Phe
    530                 535                 540

Thr Ser Glu Phe Glu Pro Ala Met Gln Ile Asp Gly
545                 550                 555


<210> SEQ ID NO 17
<211> LENGTH: 459
<212> TYPE: PRT
<213> ORGANISM: Homo sapiens

<400> SEQUENCE: 17

Met Arg Ala Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
            20                  25                  30

Phe Phe Arg Arg Ser Gln Gln Asn Asn Ala Ser Tyr Ser Cys Pro Arg
        35                  40                  45

Gln Arg Asn Cys Leu Ile Asp Arg Thr Asn Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu Tyr Ala Glu
                85                  90                  95

Val Gln Lys His Gln Gln Arg Leu Gln Glu Gln Arg Gln Gln Gln Ser
            100                 105                 110

Gly Glu Ala Glu Ala Leu Ala Arg Val Tyr Ser Ser Ser Ile Ser Asn
        115                 120                 125

Gly Leu Ser Asn Leu Asn Asn Glu Thr Ser Gly Thr Tyr Ala Asn Gly
    130                 135                 140

His Val Ile Asp Leu Pro Lys Ser Glu Gly Tyr Tyr Asn Val Asp Ser
145                 150                 155                 160

Gly Gln Pro Ser Pro Asp Gln Ser Gly Leu Asp Met Thr Gly Ile Lys
                165                 170                 175

Gln Ile Lys Gln Glu Pro Ile Tyr Asp Leu Thr Ser Val Pro Asn Leu
            180                 185                 190

Phe Thr Tyr Ser Ser Phe Asn Asn Gly Gln Leu Ala Pro Gly Ile Thr
        195                 200                 205

Met Thr Glu Ile Asp Arg Ile Ala Gln Asn Ile Ile Lys Ser His Leu
    210                 215                 220

Glu Thr Cys Gln Tyr Thr Met Glu Glu Leu His Gln Leu Ala Trp Gln
225                 230                 235                 240

Thr His Thr Tyr Glu Glu Ile Lys Ala Tyr Gln Ser Lys Ser Arg Glu
                245                 250                 255
```

```
Ala Leu Trp Gln Gln Cys Ala Ile Gln Ile Thr His Ala Ile Gln Tyr
            260                 265                 270

Val Val Glu Phe Ala Lys Arg Ile Thr Gly Phe Met Glu Leu Cys Gln
        275                 280                 285

Asn Asp Gln Ile Leu Leu Leu Lys Ser Gly Cys Leu Glu Val Val Leu
    290                 295                 300

Val Arg Met Cys Arg Ala Phe Asn Pro Leu Asn Asn Thr Val Leu Phe
305                 310                 315                 320

Glu Gly Lys Tyr Gly Gly Met Gln Met Phe Lys Ala Leu Gly Ser Asp
                325                 330                 335

Asp Leu Val Asn Glu Ala Phe Asp Phe Ala Lys Asn Leu Cys Ser Leu
            340                 345                 350

Gln Leu Thr Glu Glu Glu Ile Ala Leu Phe Ser Ser Ala Val Leu Ile
        355                 360                 365

Ser Pro Asp Arg Ala Trp Leu Ile Glu Pro Arg Lys Val Gln Lys Leu
    370                 375                 380

Gln Glu Lys Ile Tyr Phe Ala Leu Gln His Val Ile Gln Lys Asn His
385                 390                 395                 400

Leu Asp Asp Glu Thr Leu Ala Lys Leu Ile Ala Lys Ile Pro Thr Ile
                405                 410                 415

Thr Ala Val Cys Asn Leu His Gly Glu Lys Leu Gln Val Phe Lys Gln
            420                 425                 430

Ser His Pro Glu Ile Val Asn Thr Leu Phe Pro Pro Leu Tyr Lys Glu
        435                 440                 445

Leu Phe Asn Pro Asp Cys Ala Thr Gly Cys Lys
    450                 455
```

<210> SEQ ID NO 18
<211> LENGTH: 518
<212> TYPE: PRT
<213> ORGANISM: Homo sapiens

<400> SEQUENCE: 18

```
Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Arg Cys Asn Ala Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
    130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175
```

-continued

```
Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
        275                 280                 285

Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
        355                 360                 365

Tyr Asn Ala Asp Asn Arg Thr Val Phe Phe Glu Gly Lys Tyr Gly Gly
    370                 375                 380

Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
                405                 410                 415

Ile Ala Leu Tyr Thr Ala Leu Val Leu Ile Asn Ala His Arg Pro Gly
            420                 425                 430

Leu Gln Glu Lys Arg Lys Val Glu Gln Leu Gln Tyr Asn Leu Glu Leu
        435                 440                 445

Ala Phe His His His Leu Cys Lys Thr His Arg Gln Ser Ile Leu Ala
    450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
            500                 505                 510

Pro Val Gly Leu Ser Lys
        515
```